(12) United States Patent
Lu et al.

(10) Patent No.: US 8,442,924 B2
(45) Date of Patent: May 14, 2013

(54) SYSTEMS AND METHODS FOR DETECTING THE PRESENCE OF A BIOLOGICAL STATUS USING CLUSTERING

(75) Inventors: Jiuliu Lu, Homestead, FL (US); Zihua Wang, Newton, MA (US); Antonio Arevalo Reyes, Middleton, MA (US); Erik Alan Gustafson, Norwood, MA (US); John Steven Riley, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 265 days.

(21) Appl. No.: 12/944,992

(22) Filed: Nov. 12, 2010

(65) Prior Publication Data

US 2011/0131159 A1    Jun. 2, 2011

Related U.S. Application Data

(60) Provisional application No. 61/261,147, filed on Nov. 13, 2009.

(51) Int. Cl.
*G06F 15/18* (2006.01)
(52) U.S. Cl.
USPC .......................................................... 706/12
(58) Field of Classification Search ...................... 706/12
See application file for complete search history.

(56) References Cited

U.S. PATENT DOCUMENTS 5,210,015 A    5/1993    Gelfand et al.
5,487,972 A    1/1996    Gelfand et al.

(Continued)

FOREIGN PATENT DOCUMENTS

EP    1 529 847 B1    5/2005
EP    1 370 694 B1    1/2007
WO    WO 2008-129428 A2    10/2008

OTHER PUBLICATIONS

Becker, K., et al., "Does Nasal Cocolonization by Methicillin-Resistant Coagulase-Negative *Staphylococci* and Methicillin-Susceptible *Staphylococcus aureus* Strains Occur Frequently Enough to Represent a Risk of False-Positive Methicillin-Resistant *S. aureus* Determinations by Molecular Methods?" *Journal of Clinical Microbiology*, Jan. 2006, pp. 229-231, vol. 44, No. 1, Copyright 2006, American Society for Microbiology.

(Continued)

*Primary Examiner* — Michael B Holmes
(74) *Attorney, Agent, or Firm* — Kilpatrick Townsend & Stockton LLP

(57) ABSTRACT

A method for determining the presence of a biological entity. The method may include entering into a digital computer, at least a plurality of first input values associated with a first genetic element (e.g., mecA), a plurality of second input values associated with a second genetic element (femA), and a plurality of third input values associated with a third genetic element (e.g., orfX) associated with a plurality of samples. Each sample includes a first input value in the plurality of first input values, a second input value in the plurality of second input values, and a third input value in the plurality of third input values. The method also includes determining a threshold value associated with the third genetic element, separating the samples using the threshold value into a first set of samples and a second set of samples, clustering the first set of samples in a feature space defined by the first genetic element and the second genetic element, defining a first boundary space using the first set of samples, and defining a second boundary space using the second set of samples. The first and second boundary spaces differentiate a biological entity from other biological statuses. Other embodiments may also include the use of a genetic element such as SCCmec.

27 Claims, 11 Drawing Sheets

U.S. PATENT DOCUMENTS

| | | | |
|---|---|---|---|
| 5,702,895 | A | 12/1997 | Matsunaga et al. |
| 5,804,375 | A | 9/1998 | Gelfand et al. |
| 6,156,507 | A | 12/2000 | Hiramatsu et al. |
| 6,335,184 | B1 * | 1/2002 | Reyes et al. ............... 435/91.2 |
| 6,356,845 | B1 * | 3/2002 | Benson et al. ............... 702/19 |
| 6,358,519 | B1 * | 3/2002 | Waterman ............... 424/404 |
| 7,368,422 | B2 * | 5/2008 | Lei et al. ............... 514/2.9 |
| 7,527,929 | B2 | 5/2009 | McKernan et al. |
| 7,632,657 | B2 * | 12/2009 | Rambach et al. ............... 435/32 |
| 7,718,421 | B2 * | 5/2010 | Chen et al. ............... 435/288.5 |
| 7,838,221 | B2 * | 11/2010 | Huletsky et al. ............... 435/6.12 |
| 7,955,796 | B2 * | 6/2011 | Schrenzel et al. ............... 435/6.12 |
| 8,000,940 | B2 * | 8/2011 | Lu et al. ............... 702/189 |
| 8,021,614 | B2 * | 9/2011 | Huang et al. ............... 422/73 |
| 8,154,273 | B2 * | 4/2012 | Britton et al. ............... 324/71.4 |
| 8,187,812 | B2 * | 5/2012 | Zhang et al. ............... 435/6.12 |
| 8,192,995 | B2 * | 6/2012 | Zhang et al. ............... 436/66 |
| 8,229,678 | B2 * | 7/2012 | Lu et al. ............... 702/21 |
| 2004/0241824 | A1 | 12/2004 | Schrenzel et al. |
| 2009/0081663 | A1 | 3/2009 | Paitan |
| 2010/0255490 | A1 | 10/2010 | Paitan |

OTHER PUBLICATIONS

Bustin, S. A., et al., "Quantitative real-time RT-PCR—a perspective," *Journal of Molecular Endocrinology*, 2005, pp. 597-601, vol. 34, Copyright 2005, Society for Endocrinology.

Cuny, C., et al., "PCR for the identification of methicillin-resistant *Staphylococcus aureus* (MRSA) strains using a single primer pair specific for SCC*mec* elements and the neighbouring chromosome-borne *orfX*," *Clinical Microbiology and Infection*, Oct. 2005, pp. 834-837, vol. 11, No. 10, Copyright 2005 by the European Society of Clinical Microbiology and Infectious Diseases.

Farley, J. E., et al., "Comparison of the BD GeneOhm Methicillin-Resistant *Staphylococcus aureus* (MRSA) PCR Assay to Culture by Use of BBL CHROMagar MRSA for Detection of MRSA in Nasal Surveillance Cultures from an At-Risk Community Population," *Journal of Clinical Microbiology*, Feb. 2008, pp. 743-746, vol. 46, No. 2, Copyright 2008, American Society for Microbiology.

Francois, P., et al., "Rapid Detection of Methicillin-Resistant *Staphylococcus aureus* Directly from Sterile or Nonsterile Clinical Samples by a New Molecular Assay," *Journal of Clinical Microbiology*, Jan. 2003, pp. 254-260, vol. 41, No. 1, Copyright 2003, American Society for Microbiology.

"Genetic Algorithm," 13 pages, downloaded Jan. 19, 2011 from URL: http://en.wikipedia.org/wiki/Genetic_algorithms.

Heid, C. A., et al., "Real Time Quantitative PCR," *Genome Research*, 1996, pp. 986-994, vol. 6, Copyright Cold Spring Harbor Laboratory Press, Downloaded from genome.cship.org on Jan. 14, 2011, Published by Cold Spring Harbor Laboratory Press.

Heusser, R., et al., "Mosaic Staphylococcal Cassette Chromosome *mec* Containing Two Recombinase Loci and a New *mec* Complex, B2," *Antimicrobial Agents and Chemotherapy*, Jan. 2007, pp. 390-393, vol. 51, No. 1, Copyright 2007, American Society for Microbiology.

Huletsky, A., et al., "New Real-Time PCR Assay for Rapid Detection of Methicillin-Resistant *Staphylococcus aureus* Directly from Specimens Containing a Mixture of *Staphylococci*," *Journal of Clincal Microbiology*, May 2004, pp. 1875-1884, vol. 42, No. 5, Copyright 2004, American Society for Microbiology.

Ito, T., et al., "Structural Comparison of Three Types of Staphylococcal Cassette Chromosome *mec* Integrated in the Chromosome in Methicillin-Resistant *Staphylococcus aureus*," *Antimicrobial Agents and Chemotherapy*, May 2001, pp. 1323-1336, vol. 5, No. 5, Copyright 2001, American Society for Microbiology.

Ito, T., et al., "Novel Type V Staphylococcal Cassette Chromosome *mec* Driven by a Novel Cassette Chromosome Recombinase, *ccrC*," *Antimicrobial Agents and Chemotherapy*, Jul. 2004, pp. 2637-2651, vol. 48, No. 7, Copyright 2004, American Society for Microbiology.

Mullis, K.B., et al., "Specific Synthesis of DNA in Vitro Via a Polymerase-Catalyzed Chain Reaction," *Methods Enzymol*, Polymerase Chain Reaction, pp. 335-350, vol. 155, 1987.

Noto, M. J., et al., "Gene Acquisition at the Insertion Site for SCC*mec*, the Genomic Island Conferring Methicillin Resistance in *Staphylococcus aureus*," *Journal of Bacteriology*, Feb. 2008, pp. 1276-1283, vol. 190, No. 4, Copyright 2008, American Society for Microbiology.

"Receiver Operating Characteristic," 5 pages, downloaded Jan. 19, 2011 from URL: http://en.wikipedia.org/wiki/Receiver_operating_characteristic.

Riley, J., "Algorithm Development White Paper #4," Algorithm Development Research Group, Mar. 15, 1999, 17 pages, Beckman Coulter.

Sinsimer, D., et al., "Use of a Multiplex Molecular Beacon Platform for Rapid Detection of Methicillin and Vancomycin Resistance in *Staphylococcus aureus*," *Journal of Clinical Microbiology*, Sep. 2005, pp. 4585-4591, vol. 43, No. 9, Copyright 2005, American Society for Microbiology.

The International Preliminary Report on Patentability with Written Opinion for PCT/US2010/056455, mailed May 24, 2012, 9 pages.

* cited by examiner

SYSTEMS AND METHODS FOR DETECTING THE PRESENCE OF A BIOLOGICAL STATUS USING CLUSTERING

CROSS-REFERENCE TO RELATED APPLICATIONS

This application is a non-provisional of, and claims the benefit under 35 USC 119(e) of U.S. Provisional Application No. 61/261,147, filed on Nov. 13, 2009, which is herein incorporated by reference in its entirety for all purposes.

BACKGROUND

Methicillin resistant strains of *Staphylococcus aureus* (MRSA) are implicated in infections with serious outcomes including nosocomial outbreaks, and show resistance to a wide range of antibiotics, thus limiting the treatment options. Healthcare associated MRSA is of particular clinical importance, because it is not only predictably cross resistant to all penicillins and cephalosporins, but is also typically resistant to multiple other commonly used antibiotics. Treatment of MRSA infections generally requires more expensive and often more toxic antibiotics, which are normally used as the last line of defense. Therefore, rapid detection of MRSA is clinically crucial for both treatment and infection control measures.

Detection of MRSA is further complicated by the fact that MRSA can often co-colonize with multiple other related bacteria, including methicillin-sensitive *Staphylococcus aureus* (MSSA), methicillin-resistant coagulase-negative *staphylococci* (MR-CoNS) and/or methicillin-sensitive coagulase-negative *staphylococci* (MS-CoNS).

Traditional methods for the detection of MRSA in clinical microbiology laboratories involve culturing the bacteria from a sample as the first step for the isolation and differentiation of MRSA from MSSA and MR-CoNS. This approach is time-consuming and requires a minimum of 20 to 24 hours until a result is known.

A number of molecular based methods have been published for the detection of methicillin resistant *Staphylococcus aureus* (MRSA) and differentiating it from methicillin sensitive *Staphylococcus aureus* (MSSA). One such method targets two separate regions of MRSA, the mecA gene of the *Staphylococcus* cassette chromosome (SCCmec, responsible for methicillin resistance) and spa gene of *Staphylococcus aureus* (U.S. Pat. No. 5,702,895, Sinsimer, et al., Journal of Clinical Microbiology, September 2005, 4585-4591). Unambiguous detection of MRSA using this approach is hampered by the co-existence of non-*Staphylococcus aureus* strains such as methicillin resistant coagulase negative *Staphylococci* (MR-CoNS) which also harbors the mecA gene for methicillin resistance (Becker, et. al. Journal of Clinical Microbiology, January 2006, p 229-231).

A more recent molecular approach utilizes primers and probes to SCCmec and the flanking region of the *Staphylococcus aureus* genome (U.S. Pat. No. 6,156,507, Hutletsky, et. al. Journal of Clinical Microbiology, May 2004, p 1875-1884). SCCmec is a mobile genetic element that carries the mecA gene and inserts at a specific site, attBscc, at the 3'-end of the orfX gene. The left extremity of SCCmec is contiguous with the non-orfX side of attBscc, while the right extremity of SCCmec is contiguous with the orfX side of attBscc (Ito, et al., Antimicrob. Agent Chemother. 2001, 45, p 1323-1336; Ito et al., Antimicrob. Agent Chemother. 2004, 48, p 2637-2651, Noto, et al., J. Bacteriol. 2008, 190:1276-1283). This approach infers the presence of the mecA gene from the detection of the SCCmec/orfX junction. This approach requires the use of multiple primers as there have been several different types of SCCmec described. This approach is also subject to false positive results due to the presence of SCCmec cassettes that do not contain the mecA gene (Farley, et. al. Journal of Clinical Microbiology, February 2008, p 743-746) and false negative results due to newly emerged SCCmec types not covered by the assay (Heusser, et al., Antimicrob. Agents Chemother. January 2007, p 390-393).

Another approach utilizes one primer in a region of high homology across the different SCCmec types and one primer in the flanking *Staphylococcus aureus* DNA (Cuny, et al. Clin. Microbiol Infect 2005; 11:834-837, European Patent 1529847 B1). This approach is also subject to false positives as the probability of also priming of MSSA is high with primers encompassing this region.

Finally, a method has been described that positively selects for *Staphylococcus aureus* using specific antibodies and magnetic beads (Francois, et al. Journal of Clinical Microbiology, January 2003, p 254-260; European Patent 1,370,694B1). This approach enriches for *Staphylococcus aureus* but requires the use of three primer/probe sets to positively identify MRSA and reduces the possibility of detecting CoNS. The method requires a centrifugation step and a separate lysis step to recover the nucleic acid.

The commercially available MRSA assays target the SCCmec right extremity junction and orfX. Five different types and numerous subtypes of SCCmec have been identified and the potential of emergence of new SCCmec subtypes is high. In addition, it is possible that MSSA derived from MRSA might retain part of the SCCmec sequence without the mecA gene. Therefore, assays targeting the SCCmec right extreme junction with orfX are likely to give false positive results with MRSA-derived MSSA and false negative results with MRSA carrying newly emergent SCCmec types/subtypes.

Thus, current methods for detection of MRSA are laborious and, time-consuming, and may not be particularly accurate. Accordingly, there exists a need for a method and system that is fast, easy to use, reliable and capable of detecting and concurrently distinguishing a biological entity such as MRSA from other related bacteria, including MSSA, and/or MR-CoNS, or other biological entities.

BRIEF SUMMARY

Embodiments of the present invention relate to systems and methods for determining if a biological status is, or is not, present in a sample. Some embodiments of the invention can be directed to a method including detecting methicillin resistant *Staphylococcus aureus* (MRSA) in a sample which may additionally contain methicillin sensitive *Staphylococcus aureus* (MSSA), methicillin resistant coagulase-negative *staphylococci* (MR-CoNS), and/or other strains of bacteria.

One embodiment of the invention is directed to a method (of creating an analytical model) including entering into a digital computer, at least a plurality of first input values associated with a first genetic element (e.g., mecA), a plurality of second input values associated with a second genetic element (e.g., femA), and a plurality of third input values associated with a third genetic element (e.g., orfX) computer associated with a plurality of samples. Each sample includes a first input value in the plurality of first input values, a second input value in the plurality of second input values, and a third input value in the plurality of third input values. The method also includes determining a threshold value associated with the third genetic element, separating the samples using the threshold value into a first set of samples and a second set of samples, clustering the first set of samples in a feature space defined by the first genetic element and the second genetic element, defining a first boundary space using the first set of samples, and defining a second boundary space using the second set of samples. The first and second boundary spaces differentiate a biological status from other biological statuses.

Another embodiment of the invention is directed to a method of creating an analytical model, which differentiates a biological status from other biological statuses. The method includes entering, into a digital computer, at least a plurality of first input values associated with a first genetic element (e.g., mecA), a plurality of second input values associated with a second genetic element (e.g., femA), and a plurality of third input values associated with a third genetic element (e.g., SCCmec) into a digital computer. The method also comprises creating one or more intermediate values using at least the plurality of first input values and at least the second input values associated with a second genetic element using the digital computer, and creating a boundary space for the biological status using the one or more intermediate values and the plurality of third input values using the digital computer. The boundary space differentiates the biological status from other biological statuses.

Other embodiments of the invention are directed to methods for using the analytical models as well as computer readable media (e.g., non-transitory computer readable media such as memory chips and memory disks) and systems that use the analytical models.

These embodiments, as well as other embodiments, will be described in more detail later in this disclosure.

DETAILED DESCRIPTION

Figure 1:
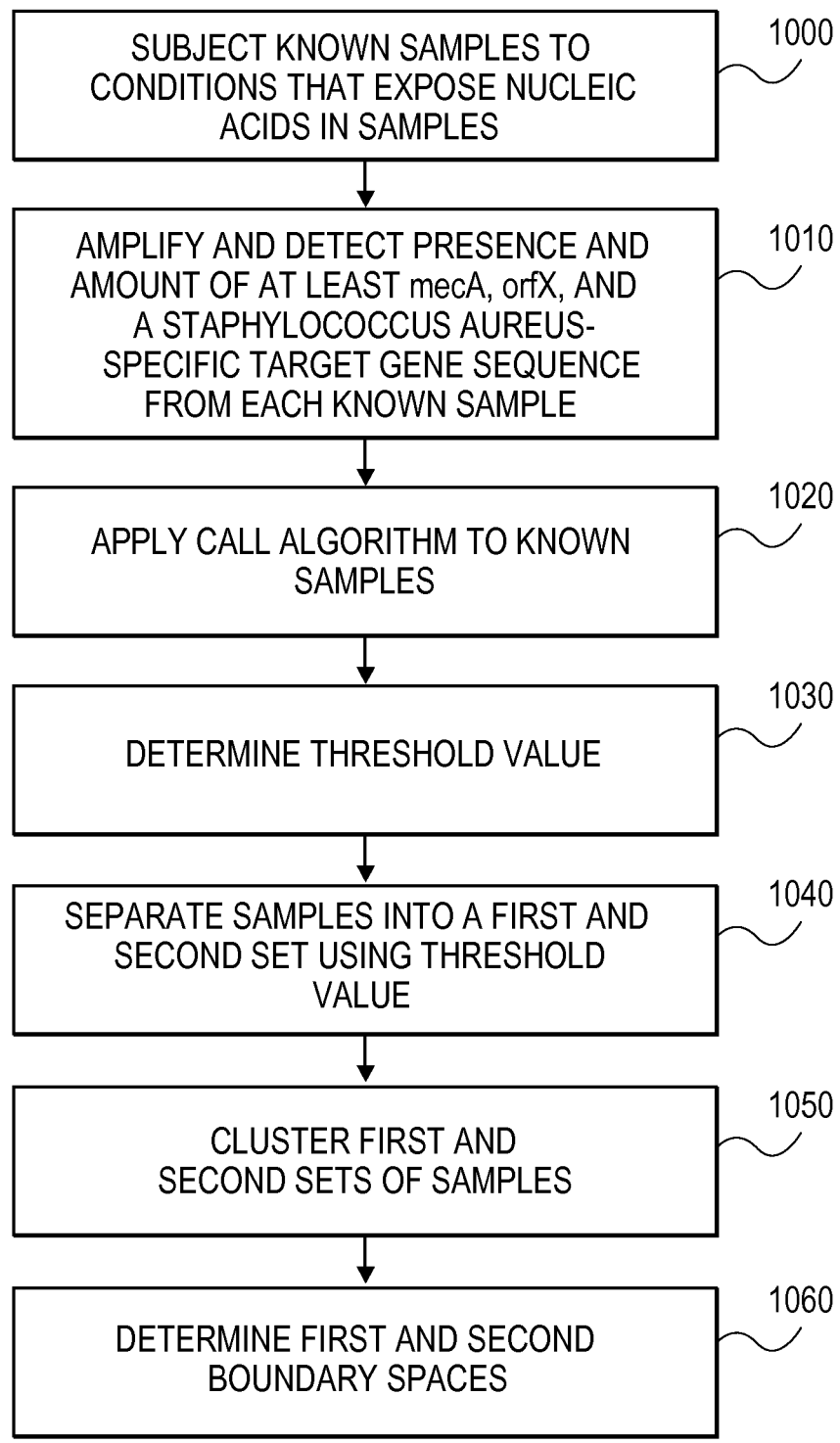
FIG. 1 shows a flowchart illustrating the steps taken according to one embodiment for forming an analytical model.

Various embodiments disclose systems and methods for identifying Methicillin resistant strains of *Staphylococcus aureus* (MRSA) in a sample from measured amounts of genetic elements such as mecA, SCCmec, orfX, and/or a *Staphylococcus aureus*-specific target gene sequence such as femA in the sample. Some embodiments of the invention determine the presence of MRSA in the sample by using a first boundary space to determine the presence of MRSA when the detected amount of orfX is below a threshold value and a second boundary space to determine the presence of MRSA when the detected amount of orfX is above the threshold value. Other embodiments create an intermediate value from at least mecA and the *Staphylococcus aureus*-specific target gene sequence and use a boundary space to determine the presence of MRSA. The boundary space can be defined using the intermediate value and SCCmec.

All scientific and technical terms used in this disclosure have meanings commonly used in the art unless otherwise specified. As used in this disclosure, the following words or phrases have the meanings specified.

As used herein, the term "sample" is used in its broadest sense, and refers to any type of material of biological origin, which can be, for example, any fluid, tissue, or cell. For example, a sample can be a biological fluid, e.g., urine, blood, serum, plasma, nasal secretion, cerebrospinal fluid, etc. Alternatively, a sample can be cultured cells or tissues, cultures of microorganisms, or any fraction or products produced from or derived from biological materials. Optionally, a sample can be purified, partially purified, unpurified, enriched or amplified.

The term "genetic element" as used herein can refer to a subsequence in a genome of interest that is useful as a target in the methods of the invention. In some embodiments, the genetic element is an open reading frame or gene, such as, for example, orfX, femA or mecA in *Staphylococcus*. A genetic element may also be a mobile genetic element, such as the *Staphylococcus* cassette chromosome, SCCmec, which may or may not comprise the mecA gene.

As used herein, "input values" may be any suitable values that can be associated with, for example, genetic elements. For example, input values can be Ct values associated that various target genes.

As used herein, a "boundary space" can be a space defined by a "boundary function." A "boundary function" can be a mathematical function that is used to determine whether data is associated with a biological status or is not associated with a biological status. Boundary functions may be created in any suitable manner including manually, by the use of neural networks, cost functions, etc. Boundary functions may also represented by any suitable shape or line, including an ellipse, rectangle, circle, or the like. Boundary functions may also be regular or irregular in shape.

As used herein, the terms "SCCmec" "SCCmec sequence" and "SCCmec cassette" are used interchangeably to refer to the genetic element known as the *Staphylococcus* cassette chromosome, which carries the mecA gene and is inserted into *Staphylococcus* sp. genome as described in Ito et al. (2001, Antimicrob. Agents Chemother. 45:1323-1336). In one embodiment, SCCmec is at an orfX junction.

The SCCmec insertion site is referred to as "orfX-ISS/attBscc" in this application. The insertion site is at the 3' end of a *Staphylococcus aureus* gene referred to herein, as "orfX". The chromosomal locus where SCCmec insertion takes place is referred to as "attBscc.". The specific sequence at the insertion site is referred to here as the "orfX-Insertion Site Sequence (orfX-ISS)" or "attBscc core region." This sequence is known to be a highly conserved sequence in

*Staphylococcus aureus* (Ito, et al., Antomicrob. Agent Chemother. 2001, 45, p 323-1336, Noto, et al., J. Bacteriol. 2008, 190:1276-1283).

After insertion into the orfX-ISS/attBscc region of *Staphylococcus aureus*, the SCCmec left extremity junction region is referred to as MRSA-LE and the right extremity junction region is referred to as MRSA-RE. In the left extremity junction, the SCCmec sequence is contiguous with the non-orfX side of attBscc. In the right extreme junction, the SCCmec sequence is contiguous with the orfX-side of attBscc. The orfX-ISS/attBscc region is described in detail in Ito et al. (2001, Antimicrob. Agents Chemother. 45:1323-1336; Ito et al., Antimicrob. Agent Chemother. 2004, 48, p 2637-2651, Noto, et al., J. Bacteriol. 2008, 190:1276-1283) and in U.S. Pat. No. 6,156,507, all of which are incorporated by reference herein. If the SCCmec insertion is not present, the orfX-ISS/attBscc region is uninterrupted. If the orfX-ISS/attBscc region is identified as intact through an amplification methodology this indicates that the SCCmec cassette has not been inserted. Lack of amplification of the orfX-ISS/attBscc region, however, does not indicate the mecA gene is present. It is known the mecA gene can be lost after the SCCmec cassette becomes inserted. Thus the SCCmec cassette can still prevent amplification of the orfX-ISS/attBscs region even in the absence of mecA.

An "oligonucleotide" is a nucleotide polymer having two or more nucleotide subunits covalently joined together. Oligonucleotides are generally about 10 to about 100 nucleotides. The sugar groups of the nucleotide subunits may be ribose, deoxyribose, or modified derivatives thereof such as OMe. The nucleotide subunits may be joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention. A "target nucleic acid" is a nucleic acid comprising a target nucleic acid sequence. A "target nucleic acid sequence," "target nucleotide sequence" or "target sequence" is a specific deoxyribonucleotide or ribonucleotide sequence that can be hybridized to a complementary oligonucleotide.

As used herein, the term "probe" refers to an oligonucleotide which is capable of hybridizing to a target nucleic acid of interest. The hybridization occurs as a result of the probe binding through complementary base pairing to a target nucleic acid of interest. It will be understood by one skilled in the art that probes will typically substantially bind target sequences lacking complete complementarity with the probe sequence depending upon the stringency of the hybridization conditions. The probe may be associated with a suitable label or reporter moiety so that the probe (and therefore its target) can be detected, visualized, measured and/or quantitated.

As used herein, the term "primer" refers to an oligonucleotide used to prime nucleic acid synthesis. A primer hyrbridizes to the template through complementary base pairing and is therefore used to initiate the replication. Hybridization occurs in the same manner as that described for probes, above. In PCR, two primers are used: a "forward primer" that typically hybridizes to the sense strand and a "reverse primer" that typically hybridizes to the antisense strand.

As used herein, the term "PCR" refers to a technique for exponential amplification of short DNA sequences (usually 50 to 600 bases) within a longer double stranded DNA molecule by enzymatic replication of DNA without using a living organism (Mullis et al. Methods Enzymol. 1987; 155:335-50). Other in vitro amplification technologies can be used in the present invention and are well known to those of skill. These methods include, for example, Ligase Chain Reaction (LCR), Nucleic Acids Sequence Based Amplification (NASBA), Strand Displacement Amplification (SDA), Transcription Mediated Amplification (TMA), Branched DNA technology (bDNA) and Rolling Circle Amplification Technology (RCAT).

As used herein the term "Real-Time PCR" refers to a type of PCR where the amplified DNA is quantified as it accumulates in the reaction in real time after each amplification cycle (Heid et al, Genome Research, 1996 6(10):986-994). A number of probe chemistries for carrying out Real-Time PCR are well known to those of skill. One commonly used method is the TaqMan® assay (see, e.g., U.S. Pat. Nos. 5,210,015; 5,487,972; and 5,804,375). Other Real-Time PCR probe chemistries that can be used and can be purchased commercially include FRET primers, Molecular Beacons, Scorpion Primers®, Amplifluor Primers®, LUX Primers®, Eclipse®, and Ultimate Probe®. For a review of Real-Time PCR techniques see Bustin et al., *J. Mol. Endocrin.* 34:597-601 (2005).

As used herein, the term "multiplex PCR" refers to a type of PCR where more than one set of primers is included in a reaction allowing two or more different targets to be amplified in a single reaction tube. The term "multiplex PCR" also refers to a PCR where multiple primers and probes are used but only one target is amplified. In one embodiment, the multiplex PCR of the present invention is a real-time PCR.

As used herein, a "biological status" may relate to a particular biological state of a sample derived from any source, for example, a patient. In most cases, the biological status relates to whether or not the sample comprises a particular biological entity, for example, a target disease organism or patient cell associated with disease. For example, one biological status may be that a sample is comprises MRSA bacteria, while another biological status may be that the sample does not comprise MRSA bacteria. In other examples, the biological status may relate to whether or not the sample comprises cancer cells.

One embodiment of the invention relates to an assay for detection of MRSA in a sample that may contain MRSA, MSSA, MR-CoNS, or other bacteria. Embodiments of the invention can utilize a multiplex PCR process for simultaneously amplifying and detecting a combination of multiple targets.

According to one embodiment, the initial amount of target DNA is measured by the PCR threshold cycle (Ct). For example, a defined signal threshold is determined for a reaction to be analyzed. The number of cycles (Ct) required to reach this signal threshold is determined for the target nucleic acid as well as for a reference or standard nucleic acid. The absolute or relative copy numbers of the target molecule can be determined on the basis of the Ct values obtained for the target nucleic acid as compared to the reference nucleic acid The Ct value is thus inversely proportional to the amount of initial target DNA, see Heid et al, 1996, Genome Research 6(10):986 for a full discussion of the Ct value which is incorporated herein by reference. Other mathematical approaches can be employed which allow for the extrapolation of the initial amount of a particular target gene based upon the indication of a predetermined set amount or number of genes amplified during one of the identified methods.

In one embodiment, the present invention is directed to a method of determining the presence of MRSA in a sample, said method comprising subjecting the sample to real-time PCR for a time and under conditions so as to generate a level of amplification product which is sufficient to be detected by fluorescence and is indicative of initial level of one or more MRSA-specific target sequences in the sample.

In another embodiment, the amplification is conducted with a set of primers (forward and reverse) and a probe. The probe may be labeled with a fluorogenic reporter molecule at its 5' end and a quenching molecule at its 3' end. The quenching molecule prevents emission of signal from the fluorogenic reporter molecule. The probe hybridizes to a region of the target sequence between the regions to which the forward and reverse primers hybridize. As the polymerase moves along the strand to which the probe has hybridized, the 5' end of the probe is cleaved off by the exonuclease activity of the polymerase thus permitting emission of the fluorogenic signal due to separation of the quenching moiety.

In specific embodiments, the probes of the invention may comprise dual-labeled fluorogenic probes comprising a fluorescent reporter (fluorophore) and a fluorescent or non-fluorescent quencher molecule. The fluorophores of the invention may be attached to the probe at any location, including the 5' terminus, the 3' terminus or internal to either termini. In an embodiment of the invention, the fluorophore and quencher are attached to the 5' and 3' termini of the probe respectively. The examples of fluorophores include, but are not limited to, FAM, ROX, HEX, NED, Cy5, Texas Red, Calfluor Red, CalFluor Orange, Quasar 670, Quasar 705. The examples of quenchers include, but are not limited to, TAMARA, Blackhole quenchers BHQ-1, BHQ-2.

In another embodiment, the invention provides a method for detecting and distinguishing MRSA from MSSA, MR-CoNS, or other bacteria utilizing a three target assay, wherein the targets (which may be examples of genetic elements) used in the assay include the mecA gene sequence, a *Staphylococcus aureus*-specific target gene sequence, an SCCmec gene sequence, and/or orfX. In a specific embodiment, the *Staphylococcus aureus*-specific target gene is femA. In the descriptions below, femA is often explicitly mentioned as the *Staphylococcus aureus*-specific target gene sequence; however, other *Staphylococcus aureus*-specific target gene sequences may also be used according to various embodiments.

Some embodiments of the invention are directed to the formation of analytical models using at least first and second boundary spaces, as well as the use of such analytical models. Other embodiments of the invention are directed to the creation and use of analytical models that use at least one intermediate value to form a boundary space. Yet other embodiments relate to methods for using such analytical models as well as systems using such analytical models. These approaches are described in further detail below.

Embodiments Using at Least Two Boundary Spaces

FIG. 1 shows a flowchart, which illustrates steps that can be used to build an analytical model according to an embodiment of the invention. In some cases, the analytical model can be used to determine whether MRSA is present in a sample.

At step 1000, a selected number of known samples are subjected to conditions that expose the nucleic acids of bacteria in the samples. In some embodiments, a known sample is one in which it is known whether or not it is associated with a particular biological status. For example, a known sample may be one where it is known whether or not sample is associated with MRSA. The known samples can thus be used to build a model that can determine whether a later unknown sample also contains MRSA.

There are many different ways for subjecting a sample to conditions that expose the nucleic acids in the sample. For example, cells in the sample may be lysed according to well known techniques. The nucleic acids may then be denatured by, for example, raising the temperature of the sample to separate strands of nucleic acids.

At step 1010, the characteristics (e.g., relative or absolute amount or amount of expression) of at least three targets, such as mecA, orfX, and a *Staphylococcus aureus*-specific target gene sequence, are measured in a sample. According to one embodiment, the *Staphylococcus aureus*-specific target gene sequence is femA. There are many different ways to measure the amounts of such genetic elements in a sample. For example, a multiplex PCR process can be used to measure the PCR threshold cycle (Ct) value for each target of the measurement.

After the characteristics of the at least three targets are measured, values associated with those characteristics may be entered into a digital computer. Details of an exemplary digital computer are provided below. The various input values may be entered into the digital computer in any suitable manner. In some embodiments, the values may be entered into the digital computer automatically (e.g., through a data connection to a measurement module that creates the input values or the data used to create the input values) or manually by a user.

In some embodiments, at least a plurality of first input values associated with a first genetic element (e.g., a first target such as mecA), a plurality of second input values associated with a second genetic element (e.g., a second target such as femA), and a plurality of third input values associated with a third genetic element (e.g., a third target such as orfX) are entered into the digital computer. The first, second, and third input values are associated with the plurality of known samples. Each known sample includes a first input value in the plurality of first input values, a second input value in the plurality of second input values, and a third input value in the plurality of third input values. The first, second and third values may be Ct values associated with the first, second, and third genetic elements.

At step 1020, a call algorithm can be applied to each of the measured targets from each of the known samples. The call algorithm can have any suitable combination of instructions. In some embodiments, the call algorithm may include one or more of the steps 1030, 1040, 1050, and 1060 in FIG. 1 in any suitable combination.

At step 1030, a threshold value associated with the third genetic element (e.g., orfX) is determined. The threshold value may be determined in any suitable manner. For example, in some embodiments, the threshold value may simply be a discrete value such as "45." The threshold value may have been previously entered into the digital computer and stored in a memory in the digital computer, or may be entered by a user at about the same time that the first input values, the second input values and the third input values are entered into the digital computer.

At step 1040, the call algorithm separates the known samples using the threshold value into a first set of samples and a second set of known samples. For example, the call algorithm may separate the first set of known samples from the second set of known samples by determining which samples fall above the threshold value and which samples fall below the threshold value. Illustratively, if the third genetic element is orfX and the threshold is a Ct value of "45," then the first set of known samples may have Ct values for orfX of less than 45 and the second set of known samples may have Ct values for orfX greater than or equal to 45.

At step 1050, after the samples are separated, the samples in the first set of samples are clustered in a feature space defined by the first genetic element and the second genetic element. The first and second set of samples may be clustered in any suitable manner. For example, the first set of samples may be plotted in two-dimensional space defined by the first genetic element and the second genetic element. The second set of samples may be plotted in two-dimensional space defined by the first genetic element and the second genetic element. This is illustrated in, for example, FIG. 2, which shows two plots of femA vs. mecA for orfX<45 and orfX>=45.

Figure 2:
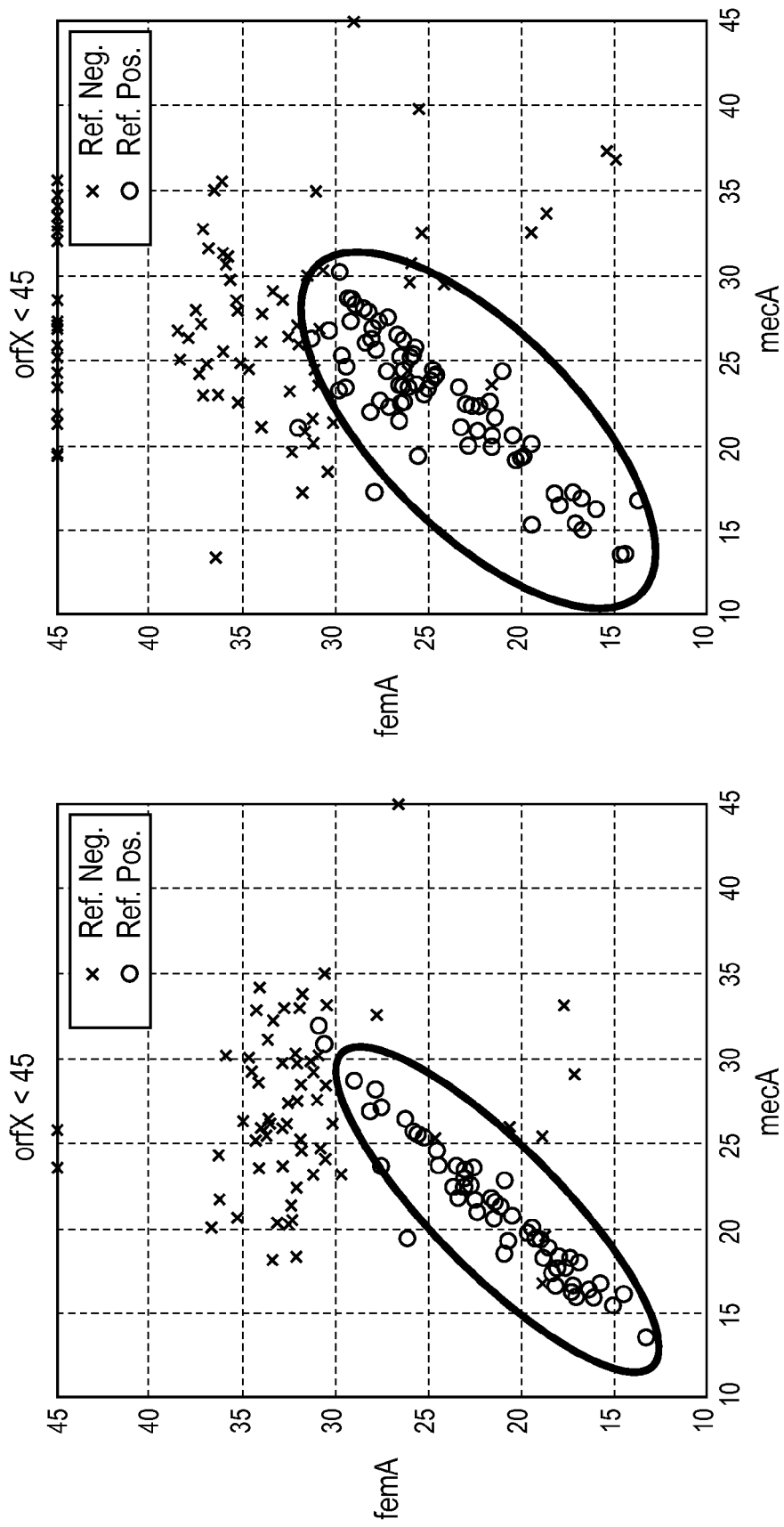
FIG. 2 shows a diagram illustrating femA vs. mecA in two-dimensional space above and below a threshold value of orfX according to one embodiment.

At step 1060, a first boundary space and a second boundary space are defined using the first and second sets of samples, respectively. The first and second boundary spaces differentiate a biological status from other biological statuses. In FIG. 2, the first and second boundary spaces are shown as ellipses.

The first and second boundary spaces can be determined in any suitable manner and can have any suitable shape. For example, in some embodiments, the first and second boundary spaces can be defined by ellipses. In other embodiments, the boundary spaces can be defined by rectangles, polygons, parallelepipeds, or other shapes. Such boundary spaces can be determined and optimized by neural networks and other optimization algorithms. The first and second boundary spaces can form at least part of an analytical model, which can be used to differentiate a biological status from other biological statuses.

In some cases, to assist a user, it may be desirable to graphically display the first and second boundary spaces over two dimensional plots including the first and second sample sets on a display such as an LCD screen.

Specific embodiments illustrating the method shown in FIG. 1 can now be described. For a 3 target "Strategy A" algorithm, 296 specimen runs were collected and provided for analytical model development. In the Strategy A implementation, the three targets corresponding to first, second, and third genetic elements included mecA, femA, and orfX.

Figure 3A:
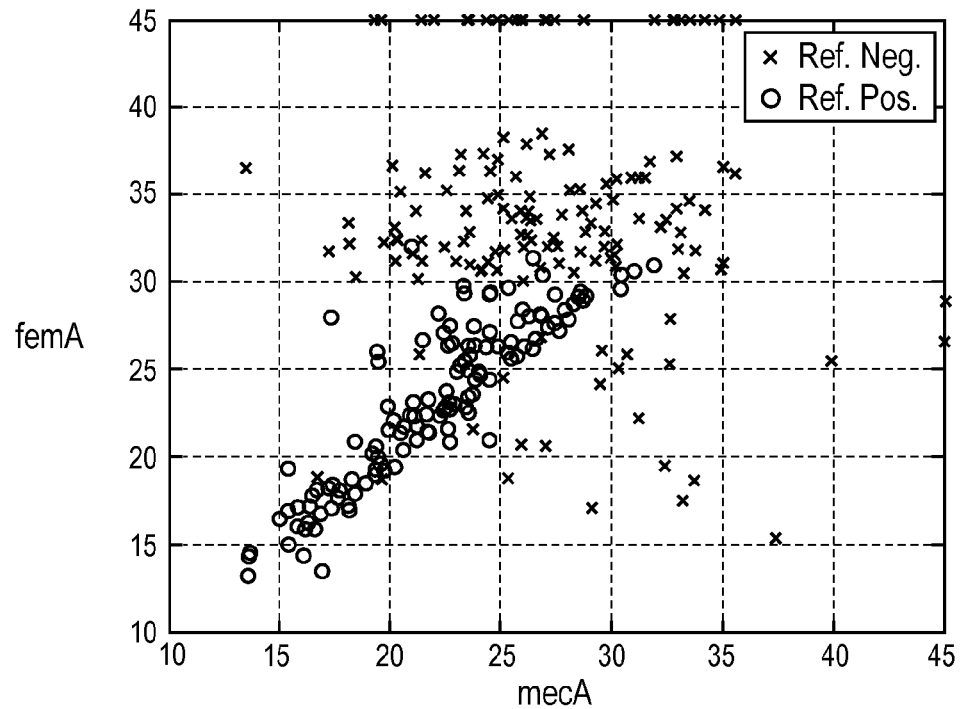
FIGS. 3A and 3B show diagrams illustrating femA vs. mecA in two-dimensional space according to one embodiment.

In any classification problem, when the appropriate characteristics are measured to distinguish one class of events from another, a unique feature space will exist that permits the data to be categorized. This is true for MRSA classification. To create the analysis routine for this application, the feature space was observed as shown in FIG. 3A. In FIG. 3A, both the positive and negative data are plotted in the femA-vs-mecA two-dimensional feature space. The positive data points cluster along the diagonal in the lower-left corner and the negative data points spread out more randomly, especially in the upper half space and lower-right corner.

Figure 3B:
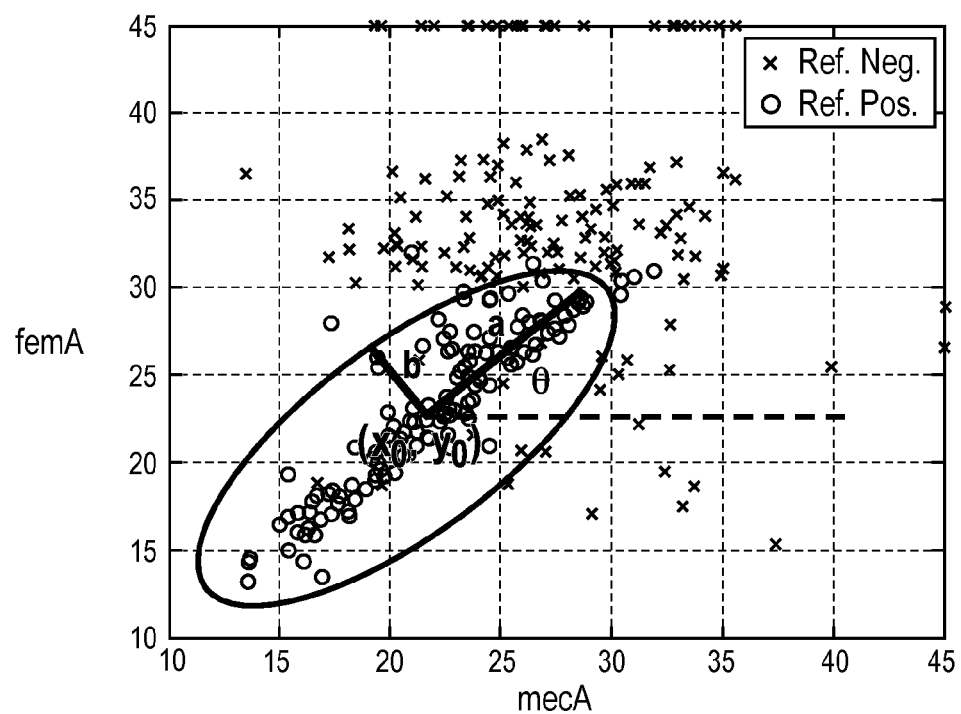

Based on this and additional confirmatory data, a mathematical model was selected to encapsulate the positive feature space. The data for the positive events resembles an ellipse which was chosen to formulate the boundary between the positive and negative clusters. An elliptic boundary can be considered an ideal selection in that positive data usually forms a Gaussian distribution in a preferred feature space (note that the cross-section of a Gaussian distribution representing the boundary of a feature space is an ellipse). This justifies the elliptical model in FIG. 3B. Mathematically, the equation for the elliptical model is given as:

$$\frac{x^2}{a^2} + \frac{y^2}{b^2} = 1,$$

where a is the semi-major axis and b is the semi-minor axis. In this instance, the ellipse is assumed to be centered about the origin. To support the MRSA detection, the elliptical model needs to support translations and angular displacement around an origin defined by $(x_0, y_0)$ and having an angle of $\theta$.

Thus, in its most general form, an ellipse can be completely characterized in a two dimensional feature space as:

$$\frac{x'^2}{a^2} + \frac{y'^2}{b^2} = 1$$

$$\text{where } \begin{cases} x' = -\cos(\theta)x + \sin(\theta)y - x_0 \\ y' = \sin(\theta)x + \cos(\theta)y - y_0 \end{cases}$$

The generalized ellipse can be governed by a set of five parameters, a, b, $x_0$, $y_0$, and $\theta$. Once the set of parameters is determined a unique ellipse (or feature space) is defined.

In order to obtain an optimal set of elliptical parameters, a cost function can be defined based on the classification results. For this type of application, a commonly used cost function is the area under curve of the receiver operating characteristic or ROC curve (refer to http://en.wikipedia.org/wiki/Receiver_operating_characteristic for more details about ROC curves). The ROC curve provides a graphical plot of the sensitivity versus the 1-Specificity for the application. For an MRSA application, a combination of the number of false positives and number of false negatives is applied as the cost function:

$$\text{cost}=c_1 *FN\#+c_2 *FP\#.$$

The weighting factors $c_1$ and $c_2$ are chosen to represent the preference in the particular problem.

Given the mathematical model for the feature space and the designed cost function definition, the model for the feature space can be optimized to minimize the cost function. The realization of the model with the minimum cost is an optimal solution for the classification problem. There are several optimization procedures that can be utilized such as Hill Climbing, Simulated Annealing, Genetic Algorithms, and so forth. For this application, a Genetic Algorithm is utilized. More detailed information about Genetic Algorithms can be found in http://en.wikipedia.org/wiki/Genetic_algorithms.

Referring to FIG. 2, it was observed that the features measured by the femA-vs-mecA in two-dimensional feature space were not always homogeneous or ideal for this model. For example, as shown in FIG. 2, when orfX is equal to or greater than 45, the positive data points forms a "fat" cluster (as outlined) but when orfX is less than 45, the positive data points forms a cluster that is more inline with an ellipse. As a result, two elliptical models are established for orfX<45 and orfX>=45, respectively. With this orfX-dependent elliptical model, the data for MRSA positive samples is essentially classified in a three-dimensional space.

The graphical depiction of the analytical model illustrated in FIG. 2 can then be used to classify unknown samples as being associated with a particular biological status such as MRSA.

Generally, the use of the formed analytical model can include entering a first input value, second input value, and third input value associated with an unknown sample into a digital computer. The digital computer may be the same digital computer that is used to form the analytical model, or may be a different digital computer (e.g., when the analytical model is formed on one digital computer, but is stored in another digital computer where it is used). The first input value, the second input value and the third input value are associated with the first, second, and third genetic elements in the unknown sample. After the input values are entered, the digital computer classifies the unknown sample as being associated with the biological status using the first boundary space or the second boundary space using the analytical model.

Figure 4:
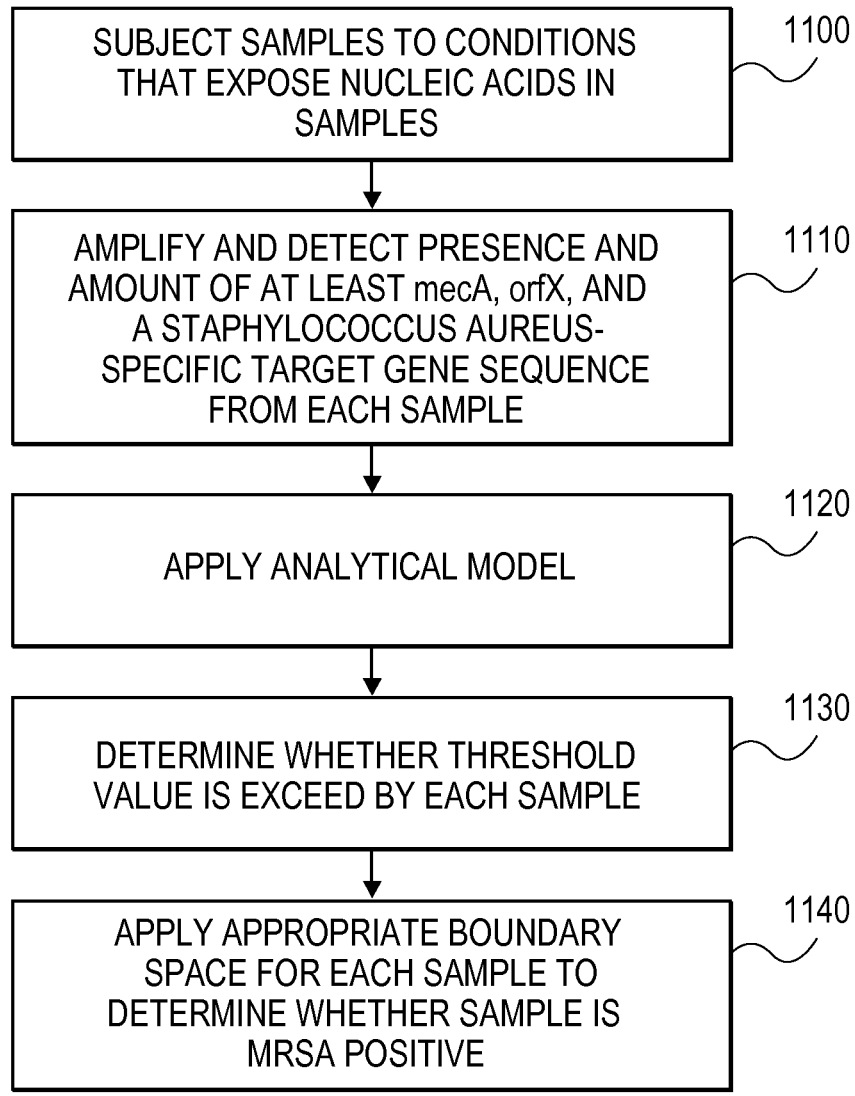
FIG. 4 shows a flowchart illustrating the steps taken according to one embodiment of using an analytical model.

FIG. 4 illustrates steps that can be used to determine whether MRSA is present in a sample according to one embodiment. As used herein, an unknown sample refers to a sample in which it is not known whether MRSA is present in the sample. The steps in FIG. 4 can use a model, such as a model created using the steps from FIG. 1, to determine whether an unknown sample contains MRSA. The unknown sample can have various targets measured, and these measurements can be used to detect the presence of MRSA by analyzing where an intermediate vector created from the measured targets of the unknown sample resides relative to a boundary function of the model.

At step 1100, the unknown sample is subjected to conditions that expose the nucleic acids of bacteria in the sample. The same techniques described above with respect to step 1000 in FIG. 1 can also be used at step 1100.

At step 1110, characteristics associated with at least three targets, mecA, fem A, and orfX, (or other genetic elements) can be determined from the unknown sample. The same techniques used during step 1010 in FIG. 1 above can be used to accomplish step 1110. The characteristics can be the same as the characteristics used to form the analytical model. For example, if Ct values are used to form the analytical model, the Ct values can be determined for the three targets in step 1110.

At step 1120, the analytical model can be applied to the input values associated with the three targets. The process associated with the analytical model can include at least steps 1130 and 1140 in FIG. 4.

At step 1130, for example, the method determines whether a third input value associated with orfX is above or below the threshold value (e.g., "45") in the analytical model.

At step 1140, if the third input value associated with the unknown sample is below a threshold value (e.g., 45), then the previously formed first boundary space is used to determine whether or not the sample is associated with the biological status of interest (e.g., MRSA). Alternatively, if the third input value associated with the unknown sample is above a threshold value (e.g., 45), then the previously formed second boundary space is used to determine whether or not the sample is associated with the biological status of interest (e.g., MRSA).

If desired, additional rules can be used to further classify the unknown sample. For example, one, two, or three or more additional targets (e.g., a target associated with MR-CoNs) may be used as additional data, which may be additionally used to classify the unknown sample.

Embodiments Using Intermediate Values

Figure 5:
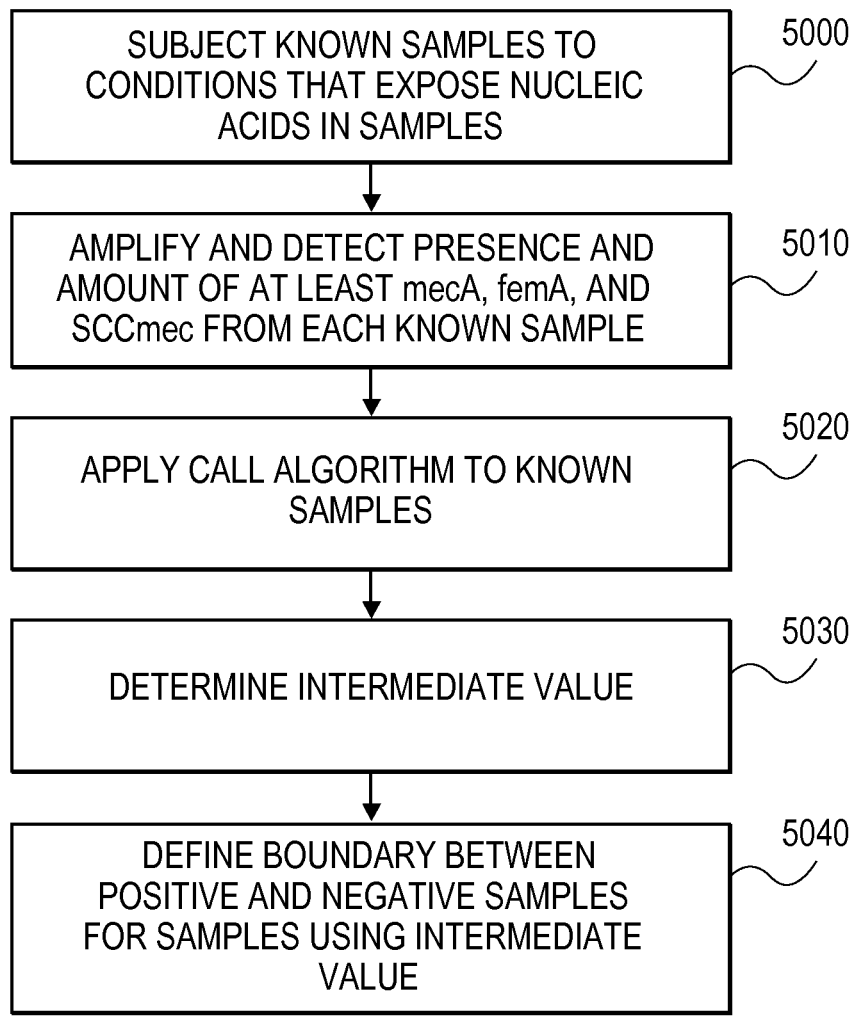
FIG. 5 shows a flowchart illustrating the steps taken according to one embodiment for forming an analytical model using an intermediate value.

Another embodiment of the invention can be directed to a method for creating an analytical model, which differentiates a biological status from other biological statuses. The method uses at least one intermediate value. Such embodiments can be described with reference to FIG. 5.

At step 5000, a selected number of known samples are subjected to conditions that expose the nucleic acids of bacteria in the samples. The details of step 5000 can be the same or different than those described with respect to step 1000 in FIG. 1, and the descriptions above need not be repeated.

At step 5010, characteristics of at least three targets, such as mecA, femA, and SCCmec, are measured for each of the known samples. The details of step 5010 can be the similar to or different than those described above with respect to step 1010 in FIG. 1, and the descriptions above need not be repeated. Note, however, that in this example, SCCmec is identified as a target instead of orfX.

After the input values are determined, they are entered into a digital computer. In some embodiments, the input values include at least a plurality of first input values associated with a first genetic element (e.g., a first target such as mecA), a plurality of second input values associated with a second genetic element (e.g., a second target such as femA), and a plurality of third input values associated with a third genetic element (e.g., a third target such as SCCmec) associated with known samples into a digital computer. The first, second, and third input values may be entered into the digital computer at any suitable time and in any suitable order.

At step 5020, a call algorithm can be applied to each of the measured targets from each of the known samples. The call algorithm in this example, is different than the call algorithm described above with respect to FIG. 1.

At step 5030, one or more intermediate values may be determined using at least the plurality of first input values and at least the second input values associated with a second genetic element using the digital computer. For example, in some embodiments, first and second input values (e.g., first and second Ct values) associated with a first genetic element (mecA) and a second genetic element (femA) may be used to create one or more intermediate values, which may be combined with the third input values associated with the third genetic element (e.g., SCCmec).

As shown in step 5040, after the one or more intermediate values are created, a boundary space for the biological status is created using the one or more intermediate values and the plurality of third input values using the digital computer. The boundary space differentiates the biological status from other biological statuses.

Illustratively, for a 3 target "Strategy C" algorithm, 199 specimen runs were collected and provided for algorithm development. In the Strategy "C" implementation, the three targets were mecA, femA, and SCCmec.

Figure 6A:
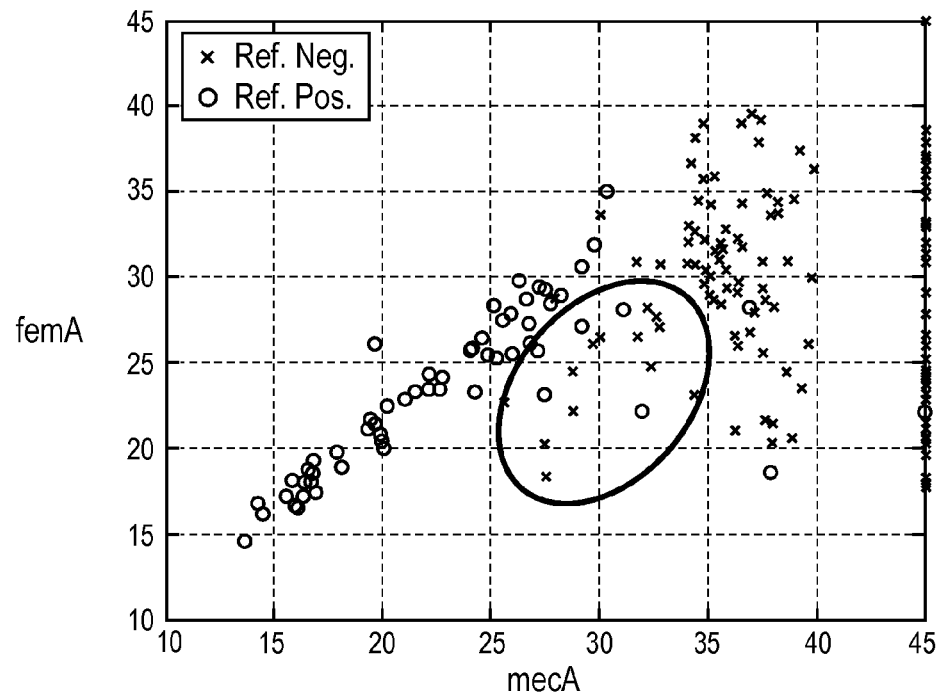
FIGS. 6A and 6B shows show diagrams illustrating mecA vs. SCCmec and femA vs. SCCmec in two-dimensional space according to one embodiment.
Figure 6B:
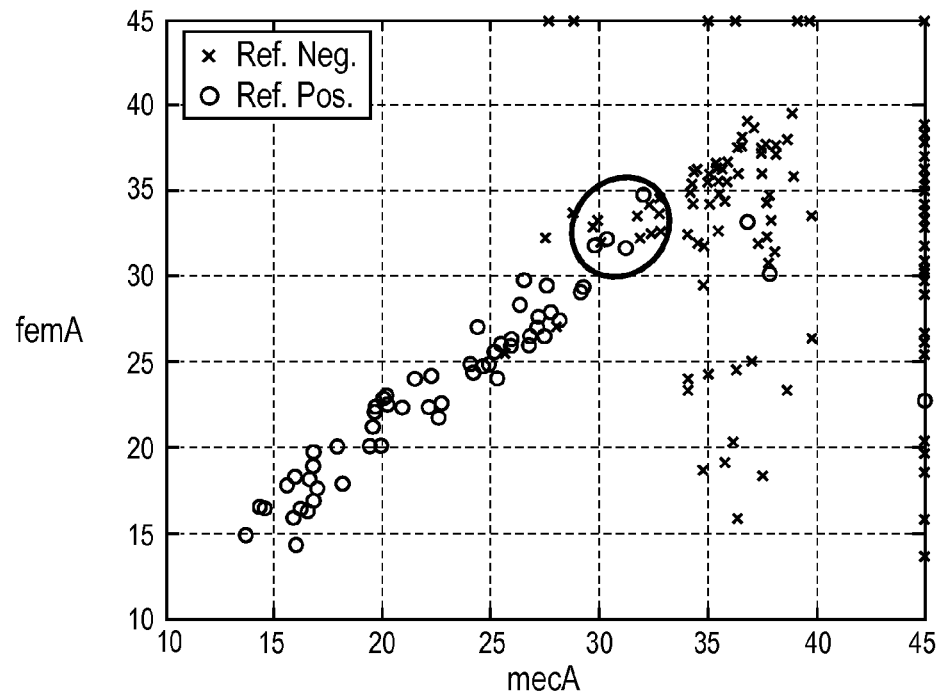

The mecA-vs-SCCmec and femA-vs-SCCmec two-dimensional feature spaces are shown in FIGS. 6A and 6B. It is observed that there is a grey area in which the positives and negatives are mixed and cannot be distinguished (outlined by the black circles) in both of the two-dimensional feature spaces.

In order to overcome the grey area, a new parameter can be used to distinguish events as positive or negative. This new parameter, was established as:

$$newParameter = mecA*\sin(-0.3) + femA*\cos(-0.3)$$

The "new parameter" is an example of an intermediate value, since it is derived from the first input values associated with a first genetic element (e.g., mecA) and second input values associated with a second genetic element (e.g., femA).

Figure 7:
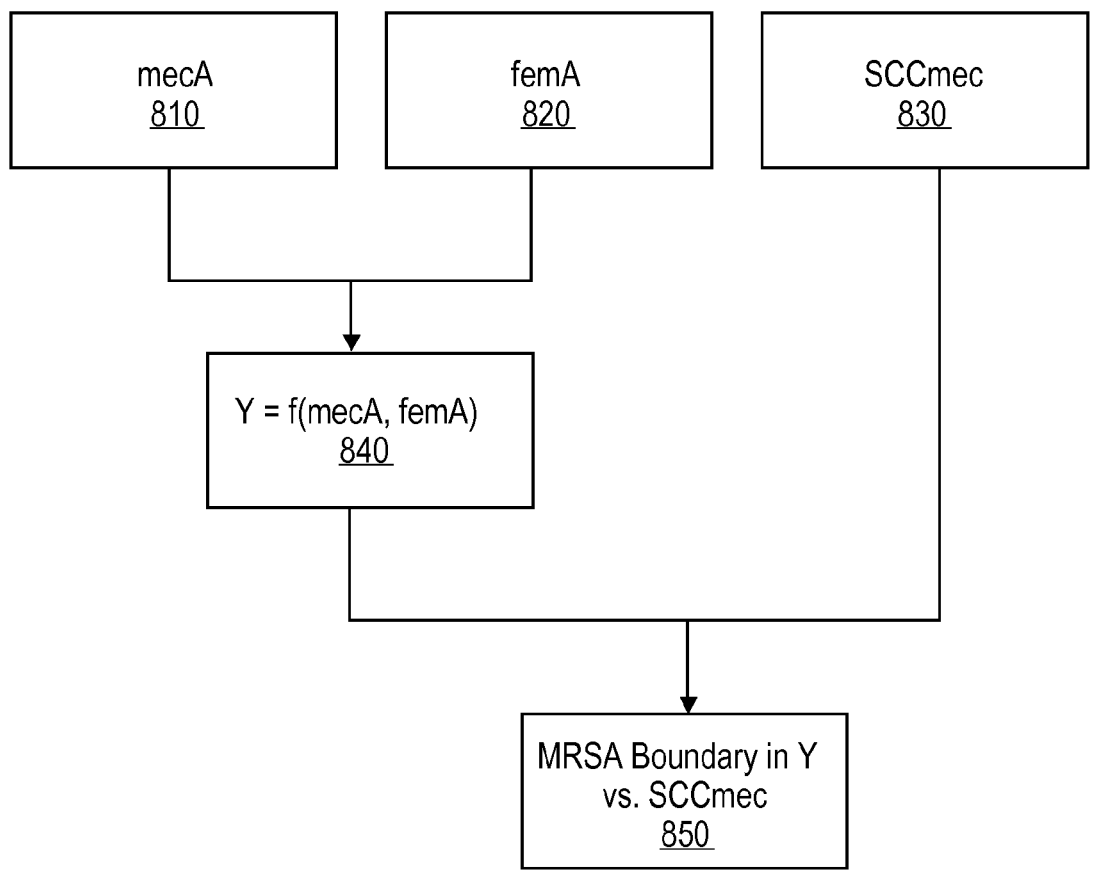
FIG. 7 shows a diagram illustrating a method for creating an intermediate value and using the intermediate value with SCCmec to create a boundary space according to one embodiment.

FIG. 7 shows an illustration of how the new parameter can be created and used. FIG. 7 shows that values associated with mecA 810 and femA 820 can be combined to form an intermediate value Y 840. This intermediate value Y 840 and SCCmec 830 can form a two dimensional feature space, which can be used to define a boundary space for the classification of unknown samples as being associated with MRSA or not MRSA.

Figure 8:
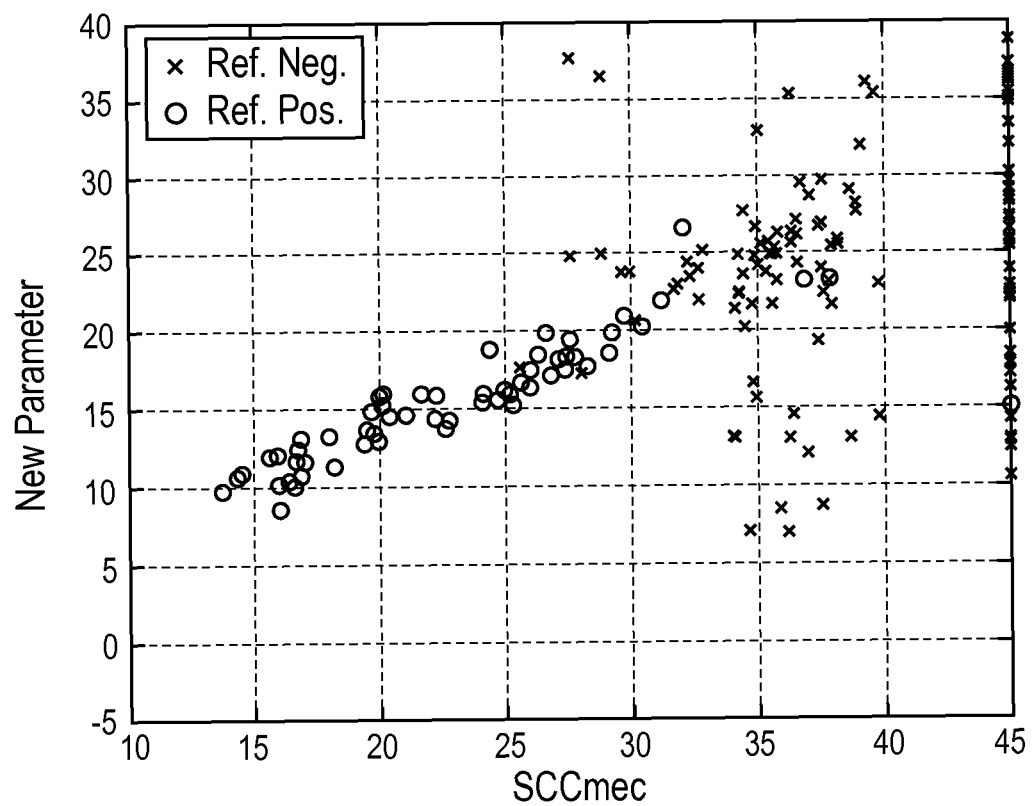
FIG. 8 shows a diagram illustrating an intermediate value vs. SCCmec in two-dimensional space according to one embodiment.

A plot of the newParameter-vs-SCCmec feature space is provided in FIG. 8. In this illustration, the grey area disappears and the new parameter, together with SCCmec, constitutes a better feature space for classification.

Figure 9:
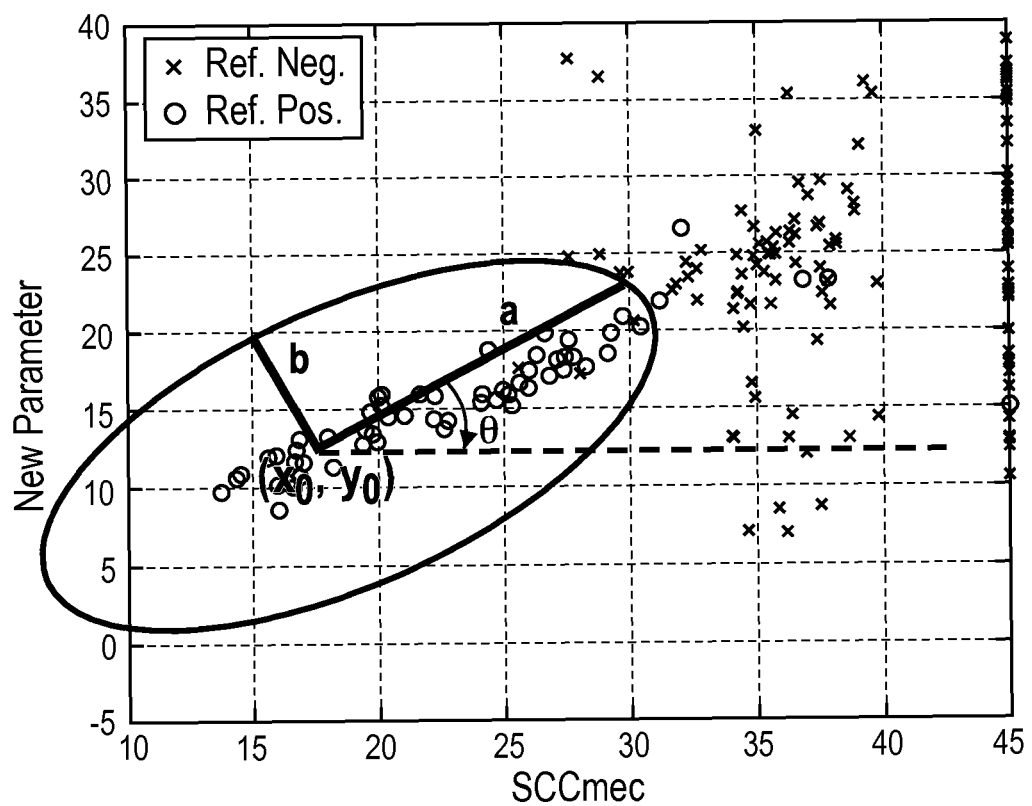
FIG. 9 illustrates a boundary space as a function of an intermediate value vs. SCCmec in two-dimensional space according to one embodiment.

Given the "newParameter" and SCCmec, an elliptical model (as shown in FIG. 9) was established to define the boundary between the positive and negative data points. The elliptical model can be optimized with a Genetic-Algorithm in the same way as previously described. (E.g., any of the previously described boundary forming techniques, such as those in step 1060 above, can be used in embodiments of the invention.) All the data points that are located inside the ellipse are deemed as MRSA positive.

Figure 10:
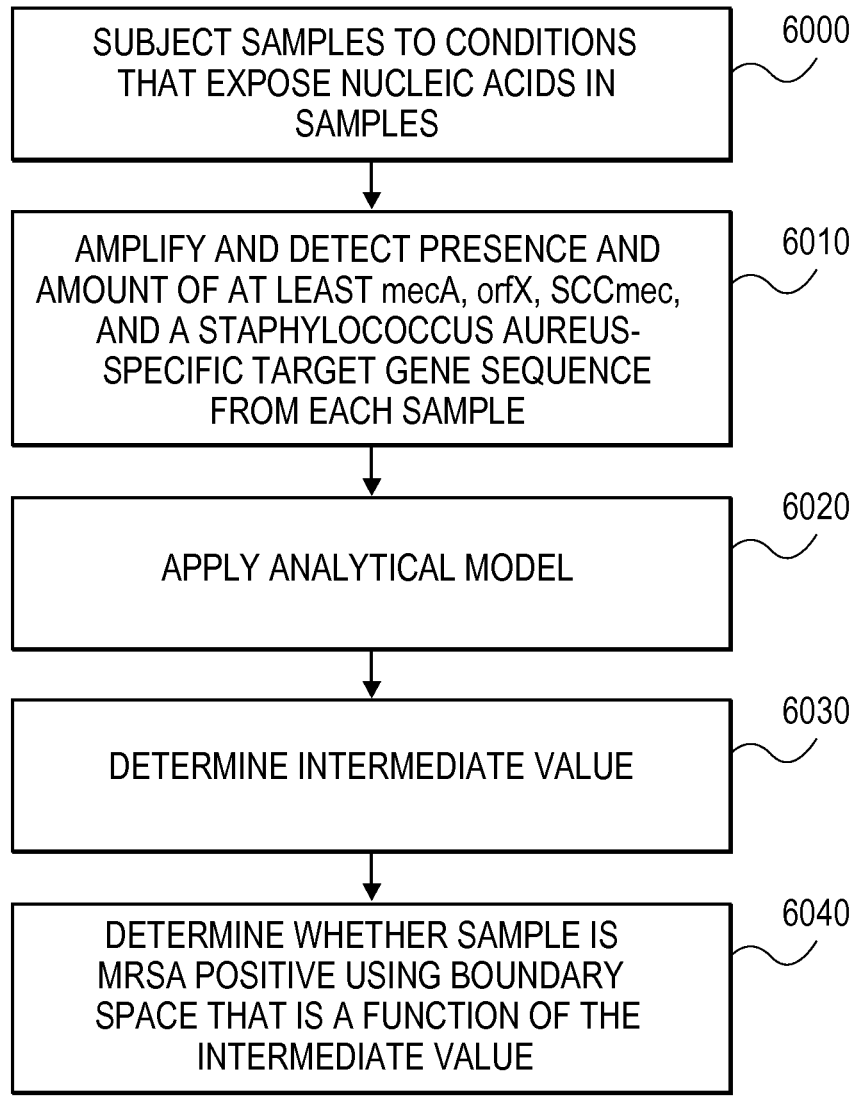
FIG. 10 shows a flowchart illustrating the steps taken according one embodiment for using an analytical model.

FIG. 10 illustrates steps that can be used to determine whether MRSA is present in a sample according to one embodiment. As used herein, an unknown sample refers to a sample in which it is not known whether MRSA is present in the sample. The method can use an analytical model, such as the model created using the steps from FIG. 5, to determine whether an unknown sample contains MRSA (or is associated with another biological status). The characteristics of various targets in the unknown sample can be measured to form first, second, and third input values. Using the input values and the analytical model, it is possible to detect the presence of MRSA in the unknown sample.

Referring to FIG. 10, at step 6000, the unknown sample is subjected to conditions that expose the nucleic acids of bacteria in the sample. The same techniques used during step 1000 in FIG. 1 can be used in step 6000.

At step 6010, characteristics of at least three targets, mecA, and SCCmec are measured from the unknown sample. First, second, and third input values can be determined for the unknown sample. The same techniques described above with respect to step 1010 can be used to accomplish step 6010.

At step 6020, analytical model and the first, second, and third input values can be used to determine whether or not the particular biological status (e.g., MRSA or not MRSA) is present in the unknown sample.

At step 6030, when applying the analytical model to the first, second, and third input values, an intermediate value can be determined using the first, and second input values. For example, the following equation could be used to determine the intermediate value:

$$Y = \text{newParameter} = \text{mecA} * \sin(-0.3) + \text{femA} * \cos(-0.3)$$

As an illustration, given a sample with mecA=28.49, femA=27.90, and SCCmec=27.26, Y=18.2345.

At step 6040, in the method, it is determined whether the sample is positive for MRSA by using the boundary function that is in the analytical model. For example, in the above example, the values Y=18.2345 and SCCmec=27.26 can be compared against the elliptical boundary function in FIG. 9. Since this example would fall inside of the boundary function, the unknown sample would be classified as MRSA positive.

Systems

Figure 11:
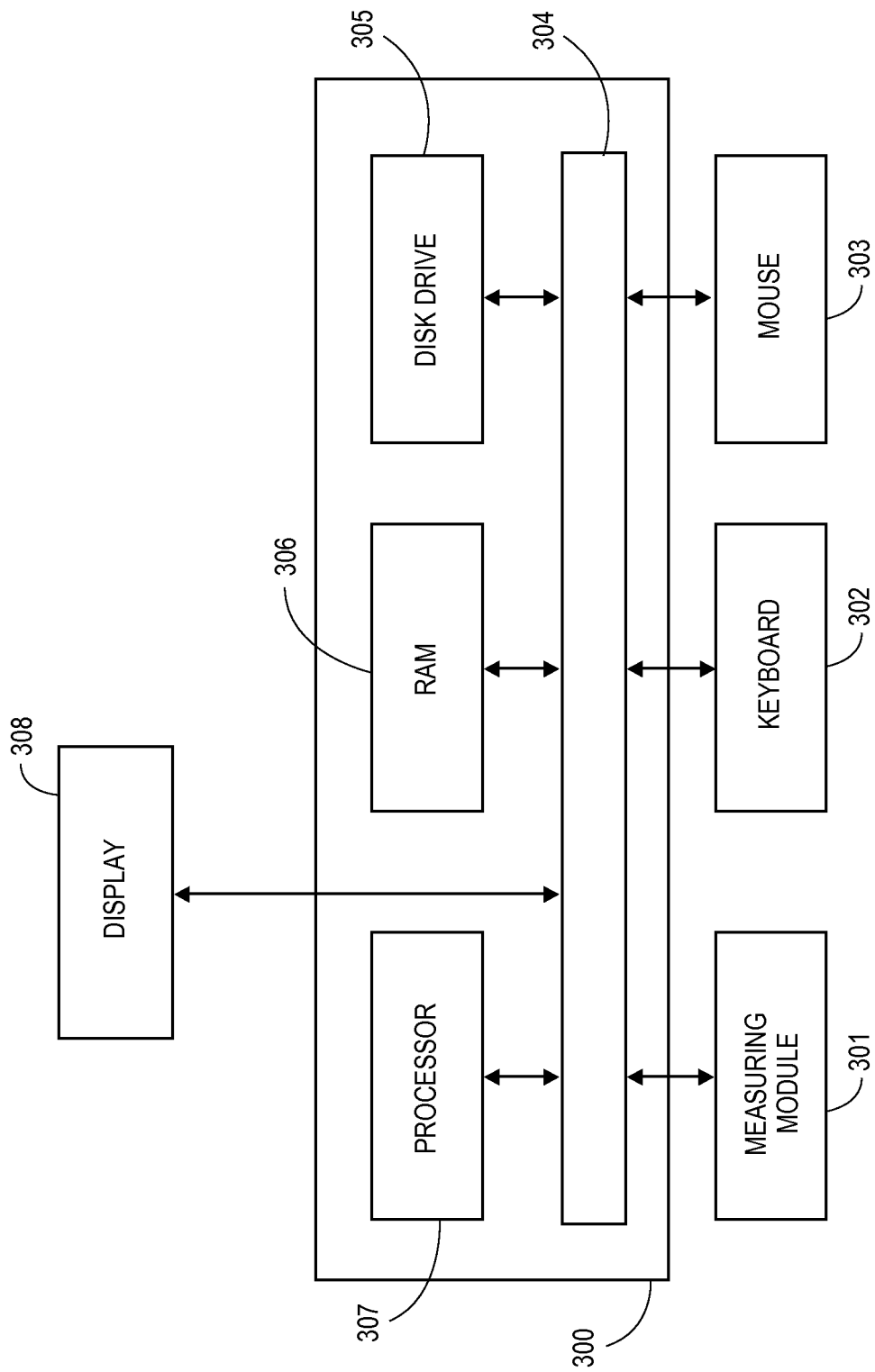
FIG. 11 is a block diagram of a system that can be used to execute various embodiments.

FIG. 11 shows a system including a digital computer 300, and a measuring module 301 operatively coupled (which may include electronic coupling) to the digital computer 300.

In this example, the digital computer 300 may include a variety of typical computer components including a system bus 304, one or more disk drives 305, RAM 306, and a processor 307, operatively coupled together. Other components can also be present depending on the exact nature of the embodiment. FIG. 11 also shows a display 308, a keyboard 302, and a mouse 303. These components and other components may also be part of the digital computer in some embodiments.

The system can also have a measuring module 301 that is used to measure characteristics of selected targets in a sample (e.g., known or unknown). This measuring module may vary between different embodiments of the invention depending on the measurement method selected to measure the target responses. For example, according to one embodiment, the measurement module may conduct a PCR analysis on a sample and may therefore be a real-time PCR apparatus. Real-time PCR apparatuses are commercially available.

In one embodiment of the invention, a sample is placed in the measurement module 301 where the sample is processed and characteristics of the selected targets (e.g., the quantities) from the sample are measured. This data (e.g., the previously described input values) is then transferred into the digital computer 300 along a system bus 304, and an appropriate call algorithm or analytical model can be applied to the response data using the processor 307. The instructions cause the processor 307 to execute the call algorithm or analytical model (as described above), which may be stored on a computer readable medium such as the RAM 306 or disk drive 305. The data representing the call algorithm and/or the analytical model can also be stored on this same media. The output from the application of the call algorithm or the analytical model can then be displayed on the display 308 or other output device (e.g., a printer). For example, the previously described boundary functions and their associated graphs may be displayed on the display 308 or output in some other manner. Thus, the information from the measured sample can then be used to either help build a model or determine whether the sample contains MRSA.

As noted above, in some embodiments, the computer readable media may store or include code which can be executed by the processor to implement a method for forming an analytical model. In one embodiment, the method may include: entering into a digital computer, at least a plurality of first input values associated with a first genetic element, a plurality of second input values associated with a second genetic element, and a plurality of third input values associated with a third genetic element into a digital computer associated with a plurality of known samples, wherein each known sample includes a first input value in the plurality of first input values, a second input value in the plurality of second input values, and a third input value in the plurality of third input values; determining a threshold value associated with the third genetic element; separating the known samples using the threshold value into a first set of known samples and a second set of known samples; clustering the first set of known samples in a feature space defined by the first genetic element and the second genetic element; defining a first boundary space using the first set of known samples, wherein the first boundary space differentiates a biological status from other biological statuses; and defining a second boundary space using the second set of known samples, wherein the second boundary space differentiates a biological status from other biological statuses. In another example, the method may include entering, into a digital computer, at least a plurality of first input values associated with a first genetic element, a plurality of second input values associated with a second genetic element, and a plurality of third input values associated with a third genetic element into a digital computer; creating one or more intermediate values using at least the plurality of first input values and at least the second input values associated with a second genetic element using the digital computer; and creating a boundary space for the biological status using the one or more intermediate values and the plurality of third input values using the digital computer, wherein the boundary space differentiates the biological status from other biological statuses.

As noted above, in some embodiments, the computer readable media may store or include code which can be executed by the processor to implement a method for using an analytical model. The method may include entering a first input value, second input value, and third input value associated with an unknown sample into the digital computer or other digital computer, wherein the first input value, the second input value and the third input value is associated with the first, second, and third genetic elements in the unknown sample; and classifying the unknown sample as being associated with the biological status using the first boundary space or the second boundary space using the digital computer or other digital computer. In another embodiment, the method may include: entering a first input value, second input value, and third input value associated with an unknown sample into the digital computer or other digital computer, wherein the first input value, the second input value and the third input value is associated with the first, second, and third genetic elements in the unknown sample; and classifying the unknown sample as being associated with the biological status using the first boundary space or the second boundary space using the digital computer or the other digital computer.

EXAMPLES 199 plurality of test samples were labeled the "Long Beach data collection." In this data collection, the following target combinations were tested: 1) orfx, mecA, and femA, 2) mecA, femA, and SCCmec, and 3) mecA, femA, SCCmec, and MR-Cons. The call algorithms developed for this data are based on a 2-dimensional elliptical mathematical model. In one example, the model generates an intermediate value. An MRSA classification result is determined by thresholding on the intermediate value. The mathematical model is formulized as $$\frac{[-x \cdot \cos(\theta) + y \cdot \sin(\theta) - x_0]^2}{a^2} + \frac{[x \cdot \sin(\theta) + y \cdot \cos(\theta) - y_0]^2}{b^2} = S,$$

where S in the intermediate value, and x and y are the two inputs to this model. For the data collection of Orfx, femA, and mecA, x and y are mecA and femA, respectively. For the data collection of SCCmec, femA, and mecA, x and y are SCCmec and Y=f(mecA, femA), respectively. To be specific, Y=f(mecA, femA)=mecA*sin(−0.3)+femA*cos(−0.3)., where −0.3 is in radian. $X_0$, $y_0$, a, b and θ are predefined parameters, which are obtained by training this model with Genetic Algorithm with a given criterion. Given $x_0$, $y_0$, a, b and θ, each pair of x and y will generate an S. A small S means that (x, y) are close to ($x_0$, $y_0$) and vice versa. For classification purposes, it is desirable to select a threshold of S (e.g., $S_0$). If a sample produces a less-than-$S_0$ intermediate value, this sample is deemed as MRSA positive. These call algorithms are based upon a parameterized mathematical model, and are trained with a genetic algorithm to reach the optimal performance, and generate classification results by thresholding on an intermediate value.

Sample Preparation

199 Nasal swabs were collected and stored in a stuart transfer medium. The swab heads were removed and each swab head was transferred into a 2 ml sample suspension tube with 1200 μL of Tris based sample buffer with 10 mM Tris pH 8.0 and 1 mM EDTA, pH 8.0~100 mg of 1 mm Zirconia/Silica beads. The bacteria on the swab heads were dislodged by vortexing the sample tubes at speed of 3000 rpm for at least 15 seconds.

The swab heads were then sterilely removed from the sample tubes and transferred into 15 ml bacteria culture tubes with 1 ml of Trypic Soy broth TSB and 6.5% NaCl. The inoculated bacteria tubes were transferred into a 37° C. incubator and incubated overnight with shaking at speed of 200 rpm.

The presence or absence of *Staphylococcus aureus* and/or MRSA was then confirmed. 10 μL of each of the overnight culture broths was streaked on BBL™ CHROMagar MRSA and a BBL™ CHROMagar *Staphylococcus aureus* plate. 500 μL of the 1200 μL sample solution from each tube was then subjected to DNA isolation procedure as described by Agencourt VirNA kit protocol. This procedure, in brief, began with 200 CFU *S. felis* bacteria as process control. 10 units of Achrompeptidase were added to each tube, mixed well, and incubated in a 70° C. waterbath for 4 minutes. A fresh prepared lysis solution 289 μL containing 188 μL of lysis buffer, 1.0 μL of PolyA (600 μg/ml), and 100 μL of protease K (6.4 mg/ml) was then added to each sample and mixed well. Each sample was then incubated at 70° C. for 1 minute and then allowed to cool for 2 minutes. Then, 10 μL of magnetic beads and 575 μL of 100% isopropanol were added and mixed well by vortexing. The reaction contents were allowed to incubate at room temperature for 5 minutes, and then the magnetic beads were collected by placing the sample tube on a magnet stand for 6 minutes to separate the magnetic beads from the sample solution until the solution become clear.

Next, the supernatant was aspirated off the samples while being careful not to remove any beads during aspiration. 500 μL of washing buffer (3.3M Guanidine Thiocyanate, 1.7% Triton X-100, 167.5 mM Sodium Citrate) were added to the samples and vortexed for 10 seconds to mix. The tubes were then incubated on the magnet for 4 minutes (or until clear). The supernatant was then aspirated off the samples again. 900 μL of 75% freshly prepared ethanol was then added and vortexed for 10 seconds. The tubes were then incubated on the magnet for 4 minutes until clear. The supernatant was then aspirated off the samples again and the ethanol washing was repeated one more time. The beads were then dried on the magnet for 15-25 minutes. When the ring of the beads started to crack, the sample was eluted. The tubes were taken off the magnet and 25 μL of nuclease free water was added. The samples were then vortexed to mix. The tubes were then incubated for 5 minutes at 70° C. The tubes were placed back on the magnet and incubated for 1 minute. The supernatant was then transferred to a clean tube for PCR amplification.

PCR Primers and Probes, PCR Cycling Conditions

The reagents listed in the Master mix table were prepared on ice. According to the total reaction number, enough Master mix can be prepared by simply adding the indicated volumes of reagents together in a DNA/RNA/RNase-free tube. The tubes can be vortexed to mix and then left on ice for later use. 20 μL of each eluent was added to a Mx3000P 96-well PCR plate (non-skirted) (Stratagene, Cat#401333) (one eluent, one well). 30 μL Master mix was added to each well filled with the eluent, and then mixed by gently pipetting up and down 8 times or more (a multi-channel might be useful.). The plate was covered tightly with MicroAmp™ optical adhesive film (Applied Biosystems), and then centrifuged at 1100×g for 3 minutes before it is put into the PCR machine.

The PCR cycling conditions on the Stratagene MX3005P instrument were set as follows: 4' @ 37° C. (1×); 1 min @ 95° C. (1×); 15 sec @ 95° C.→10 sec @62° C. 430 sec @ 58° C. (40×). The targets monitored are represented in Table 1 below:

| Target | Function | Oligo ID | Sequence (SEQ ID NO:) |
|---|---|---|---|
| orfX-ISS | Forward primer | OrfX-ISS/attBSc-c for-1 | TGAGGGTTGTGTTAATTGAGCAAGTG (1) |
| | Forward primer | OrfX-ISS/attBSc-c for-2 | TGCGGGTTGTGTTAATTGAACAAGTG (2) |
| | Reverse primer | mecII512-sccmec-3 | TCACTTTTTATTCTTCAAAGATTTGAGC (3) |
| | Reverse primer | primer 11-1-sccmec-7 | AAATTGCTACTAAAGAGGATATGGAAAACCATC (4) |
| | Reverse primer | primer12-sccmec-8 | CTCTGCTTTATATTATAAAATTACGGCTG (5) |
| | Reverse primer | newtypeiii-1-sccmec-14 | CGTATGATATTGCAAGGTATAATCCAATATTTC (6) |
| | Reverse primer | typeIVc-sccemc-2 | CTTGAAATGAAAGACTGCGGAGGCTAAC (7) |
| | Reverse primer | NEWPRIMERS | TGAGCTTTTCCACTCCCATTTCTTCCAAA (8) |
| | Reverse primer | SCCmec-4nV | GCAATTCACATAAACCTCATATGTTCTGATAC (9) |
| | Reverse primer | SCCmec-3n | CATTCATTCATCCACCCTAAACTTAATCTTTC (10) |
| | Reverse primer | SCCmec-5n | TATGGAAATCCATCTCTACTTTATTGTTTTCTTC (11) |
| | Reverse primer | SCCmec-6n | AATATTTCATATATGTAATTCCTCCACATCTC (12) |
| | Reverse primer | SE-7-11 | CTATTTCTGTAATACTTAAAACCTTTTCTTCC (13) |
| | Reverse primer | SE-17 | CCGTATGATTCATATTAAAATGAATCATACGGAGG (14) |
| | Reverse primer | SE-13 | CTTCTTATGAAATGTCTTTTTTCACTTATCC (15) |
| | TaqMan probe | orfx probe-2 | ATGCTTCTCCTCGCATAATCTTAAAYGCTC (16) |
| | TaqMan probe | ORFX PROBE-1 | ACGCTTCTCCACGCATAATCTTAAATGCTC (17) |
| | TaqMan probe | ORFX PROBE | ACGCCTCTCCTCGCATAATCTTAAATGCTC (18) |
| femA | Forward primer | femA-3 forward primer | GACCGTTATAATTTCTATGGTGTTAGTGG (19) |
| | Reverse primer | femA-3 reverse primer | GTCACCAACATATTCAATAATTTCAGC (20) |
| | TaqMan probe | femA-sa-probe | ACAGAAGATGCTGAAGATGCTGGTGT (21) |
| mecA | Forward primer | mecA-2 forward primer | GCAGAAAGACCAAAGCATACATATTGA (22) |
| | Reverse primer | MecA-2 reverse primer | GCCTATCTCATATGCTGTTCCTGT (23) |
| | TaqMan probe | mecAprobe | AGACCGAAACAATGTGGAATTGGCCA (24) |
| S. felis (IC) | IC forward primer | Sfforwardnew | TGCCAATGTAGATAGTCTTCCAGA (25) |
| | IC reverse primer | sfreversenew | AAGTGCCCAGAAGAATGAGTGG (26) |
| | IC probe | fSfelis | ACCGCCACCATTATTACGTACAGCTG (27) |
| SCCmec | Forward primer | OrtX-ISS/attBSc-c for-1 | TGAGGGTTGTGTTAATTGAGCAAGTG (1) |
| | Forward primer | OrtX-ISS/attBSc-c for-2 | TGCGGGTTGTGTTAATTGAACAAGTG (2) |
| | Reverse primer | mecII512-1-sccmec-3 | TCACTTTTTATTCTTCAAAGATTTGAGC (3) |
| | Reverse primer | primer11-1-sccmec-7 | AAATTGCTACTAAAGAGGATATGGAAAACCATC (4) |
| | Reverse primer | primer12-sccmec-8 | CTCTGCTTTATATTATAAAATTACGGCTG (5) |
| | Reverse primer | newtypeiii-1-sccmec-14 | CGTATGATATTGCAAGGTATAATCCAATATTTC (6) |
| | Reverse primer | typeIVc-sccemc-2 | CTTGAAATGAAAGACTGCGGAGGCTAAC (7) |
| | Reverse primer | NEWPRIMERS | TGAGCTTTTCCACTCCCATTTCTTCCAAA (8) |
| | Reverse primer | SCCmec-4nV | GCAATTCACATAAACCTCATATGTTCTGATAC (9) |
| | Reverse primer | SCCmec-3n | CATTCATTCATCCACCCTAAACTTAATCTTTC (10) |
| | Reverse primer | SCCmec-5n | TATGGAAATCCATCTCTACTTTATTGTTTTCTTC (11) |
| | Reverse primer | SCCmec-6n | AATATTTCATATATGTAATTCCTCCACATCTC (12) |
| | Reverse primer | SE-7-11 | CTATTTCTGTAATACTTAAAACCTTTTCTTCC (13) |
| | Reverse primer | SE-17 | CCGTATGATTCATATTAAAATGAATCATACGGAGG (14) |
| | Reverse primer | SE-13 | CTTCTTATGAAATGTCTTTTTTCACTTATCC (15) |
| | TaqMan probe | orfx probe-2 | ATGCTTCTCCTCGCATAATCTTAAAYGCTC (16) |
| | TaqMan probe | ORFX PROBE-1 | ACGCTTCTCCACGCATAATCTTAAATGCTC (17) |
| | TaqMan probe | ORFX PROBE | ACGCCTCTCCTCGCATAATCTTAAATGCTC (18) |

In the table above, the probes that have sequences that correspond to SCCmec are complementary to the right extremity of SCCmec.

The table below shows false positive and false negative data generated using 199 samples in the Long Beach data collection and using analytical models according to embodiments of the invention (as described above) and analytical models using other call algorithms.

| Enrichment Culture Data 1 (59 pos, 140 neg) | | | |
|---|---|---|---|
| | FP | FN | |
| 1: Strategy A 3-Target clustering (mecA, femA, orfX) | 10 | 2 | DxN calling algorithm |
| 2: Strategy C 4-Target clustering (mecA, femA, SCCmec (MRSA), SCCmec (MR-ConS)) | 3 | 2 | DxN calling algorithm |
| 3: Strategy C 3-Target clustering (mecA, femA, SCCmec) | 3 | 4 | DxN calling algorithm |
| 4: Xpert-1 Target (SCCmec) | 11 | 2 | |
| 5: Strategy C 1-Target (SCCmec) | 11 | 4 | Published call algorithm |
| 6: Strategy C 2-Target (SCCmec, mecA) | 10 | 5 | Published call algorithm |
| 7: Strategy C (SCCmec, mecA) Ct comparison (±4ct) | 5 | 7 | Published call algorithm |
| 8: Strategy C 2-Target (SCCmec, femA) | 3 | 5 | Published call algorithm |
| 9: Strategy C (SCCmec, femA) Ct Comparison | 3 | 5 | Published call algorithm |
| 10: Strategy C 3-Target (SCCmec, mecA and femA) | 2 | 5 | Published call algorithm |
| 11: Strategy A 2 target (femA and mecA) | 38 | 1 | Published call algorithm |
| 12: Strategy A 2 target (orfX - ve) Ct comparison (±4ct) | 24 | 5 | Published call algorithm |
| 13: Strategy A 3 targets (mecA, femA, orfX) | 18 | 25 | Published call algorithm |
| 14: Strategy A 3 targets (mecA, femA, orfX) Ct comparison (±4ct) | 17 | 5 | Published call algorithm |

The first three analytical models (1 to 3) are those produced according to embodiments of the invention, and show good results. The first analytical model entitled Strategy A using three target clustering and the process described above (e.g., as in FIG. 1) yielded 10 false positives and 2 false negatives. The second analytical model using Strategy C and 4 targets yielded 3 false positives and 2 false negatives. The third analytical model using Strategy C yielded 3 false positives and 4 false negatives. The methods associated with Strategy A and Strategy C are described above (e.g., as in FIG. 5). In the case of the 4 target Strategy C example, MRConS was used as additional target to differentiate MRSA samples from non-MRSA samples.

The remaining data shows data that was processed according to published call algorithms. Some of the details of such algorithms are provided below.

For 4: Xpert is a known and commercially available test.

For 5: Strategy C 1-target; SCCmec is the target. If an SCCmec Ct value is less than 32, then MRSA is present. If the SCCmec Ct value is larger than 32, then there is no MRSA.

For 6: Strategy C 2-Target (SCCmec, mecA): If both SCCmec and mecA are less than 32, then MRSA is present. If SCCmec is larger than 32 or mecA larger than 32, then there is no MRSA.

For 7: Strategy C (SCCmec, mecA) Ct comparison (±4 ct): If SCCmec is larger than 32 or mecA is larger than 32, then there is no MRSA. If both SCCmec and mecA Ct values are less than 32, and the delta Ct between SCCmec and mecA is less than 4, then MRSA is present. If the delta Ct is larger than 4, then MRSA is not present.

For 8: Strategy C 2-Target (SCCmec, femA): If both SCCmec and femA are less than 32, then MRSA is present. If SCCmec is larger than 32 or femA is larger than 32, then there is no MRSA.

For 9: Strategy C (SCCmec, femA) Ct Comparison: If SCCmec is larger than 32 or femA is larger than 32, then there is no MRSA. If both SCCmec and femA Ct values are less than 32, and the delta Ct between SCCmec and femA is less than 4, then MRSA is present. If the delta Ct is larger than 4, then MRSA is not present.

For 10: Strategy C 3-Target (SCCmec, mecA and femA): If SCCmec, mecA, femA are larger than 32, then MRSA is not present. If mecA is larger than 32, then there is no MRSA. If SCCmec is larger than 32, then no MRSA is present. If mecA and femA are both less than 32, and SCCmec is larger than 32, and the delta Ct value of mecA and femA is less than 4, MRSA is present.

For 11: Strategy A 2 target (femA and mecA): If both femA and mecA are less than 32, then MRSA is present. Otherwise, there is no MRSA.

For 12: Strategy A 2 target (orfX-ye) Ct comparison (±4 ct): If both femA and mecA are less than 32 and the delta Ct between femA and mecA is less than 4, then MRSA is present. Otherwise, there is no MRSA.

For 13: Strategy A 3 targets (mecA, femA, orfX):): If both femA and mecA are less than 32 and orfX is negative, then MRSA is present. Otherwise, there is no MRSA.

For 14: Strategy A 3 targets (mecA, femA, orfX) Ct comparison (±4 ct):): If both femA and mecA are less than 32 and orfX is negative, and the delta Ct value between mecA and femA is less than 4, then MRSA is present. Otherwise, there is no MRSA.

The software components, steps, or functions described in this application, may be implemented as software code to be executed by one or more processors using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may also reside on or within a single computational apparatus, and may be present on or within different computational apparatuses within a system or network.

Some embodiments of the present invention can be implemented in the form of control logic in software or hardware or a combination of both. The control logic may be stored in an information storage medium as a plurality of instructions adapted to direct an information processing device to perform a set of steps disclosed in an embodiment of the present invention. Based on the disclosure and teachings provided herein, a person of ordinary skill in the art will appreciate other ways and/or methods to implement the present invention.

Any recitation of "a", "an" or "the" is intended to mean "one or more" unless specifically indicated to the contrary.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

All patents, patent applications, publications, and descriptions mentioned above are herein incorporated by reference in their entirety for all purposes. None is admitted to be prior art.

What is claimed is:

1. A method for determining the presence of methicillin-resistant *Staphylococcus aureus* (MRSA) in a sample, the method comprising:
   subjecting the sample to conditions that will expose the nucleic acids of any bacteria present in the sample;
   amplifying and detecting the presence and amounts of at least mecA, orfX, and a *Staphylococcus aureus*-specific target gene sequence in the sample; and
   determining the presence of MRSA in the sample by executing a call algorithm on a digital computer, wherein the call algorithm uses as inputs at least the detected and measured amounts of mecA, orfX, and the *Staphylococcus aureus*-specific target gene sequence to determine whether MRSA is present in the sample, wherein the call algorithm uses a first boundary space to determine the presence of MRSA when the detected amount of orfX is below a threshold value, wherein the call algorithm uses a second boundary space to determine the presence of MRSA when the detected amount of orfX is above the threshold value.

2. A system for determining the presence of methicillin-resistant *Staphylococcus aureus* (MRSA) in a sample, the system comprising:
   a measuring module capable of amplifying and detecting the presence and amounts of at least mecA, orfX, and a *Staphylococcus aureus*-specific target gene sequence in the sample, wherein the sample has been subjected to conditions that will expose the nucleic acids of any bacteria present in the sample;
   a memory to store the detected amounts from the measuring module;
   a computer readable medium containing computer readable code having instructions for executing a call algorithm, wherein the call algorithm uses as inputs at least the detected and measured amounts of mecA, orfX, and the *Staphylococcus aureus*-specific target gene sequence to determine whether MRSA is present in the sample, wherein the call algorithm uses a first boundary space to determine the presence of MRSA when the detected amount of orfX is below a threshold value, wherein the call algorithm uses a second boundary space to determine the presence of MRSA when the detected amount of orfX is above the threshold value; and
   a processor to execute the computer readable code on the computer readable medium in order to determine the presence MRSA in the sample.

3. A computer-readable medium comprising:
   code for a call algorithm, wherein the call algorithm uses as inputs at least the detected and measured amounts of mecA, orfX, and a *Staphylococcus aureus*-specific target gene sequence to determine whether MRSA is present in the sample, wherein the call algorithm uses a first boundary space to determine the presence of MRSA when the detected amount of orfX is below a threshold value, wherein the call algorithm uses a second boundary space to determine the presence of MRSA when the detected amount of orfX is above the threshold value.

4. A method for determining the presence of methicillin-resistant *Staphylococcus aureus* (MRSA) in a sample, the method comprising:
   subjecting the sample to conditions that will expose the nucleic acids of any bacteria present in the sample;
   amplifying and detecting the presence and amounts of at least mecA, SCCmec, and a *Staphylococcus aureus*-specific target gene sequence (SA) in the sample; and
   determining the presence of MRSA in the sample by executing a call algorithm on a digital computer, wherein the call algorithm uses as inputs at least the detected and measured amounts of mecA, SCCmec, and the *Staphylococcus aureus*-specific target gene sequence to determine whether MRSA is present in the sample, wherein the call algorithm creates an intermediate value from at least the *Staphylococcus aureus*-specific target gene sequence and mecA, wherein the call algorithm further uses a boundary space to determine the presence of MRSA, wherein the boundary space is defined using the intermediate value and SCCmec.

5. A system for determining the presence of methicillin-resistant *Staphylococcus aureus* (MRSA) in a sample, the system comprising:
   a measuring module capable of amplifying and detecting the presence and amounts of at least mecA, SCCmec, and a *Staphylococcus aureus*-specific target gene sequence (SA) in the sample, wherein the sample has been subjected to conditions that will expose the nucleic acids of any bacteria present in the sample;
   a memory to store the detected amounts from the measuring module;
   a computer readable medium containing computer readable code having instructions for executing a call algorithm, wherein the call algorithm uses as inputs at least the detected and measured amounts of mecA, SCCmec, and the *Staphylococcus aureus*-specific target gene sequence to determine whether MRSA is present in the sample, wherein the call algorithm creates an intermediate value from at least mecA and the *Staphylococcus aureus*-specific target gene sequence, wherein the call algorithm further uses a boundary space to determine the presence of MRSA, wherein the boundary space is defined using the intermediate value and SCCmec; and
   a processor to execute the computer readable code on the computer readable medium in order to determine the presence MRSA in the sample.

6. A computer-readable medium comprising:
   code for a call algorithm, wherein the call algorithm uses as inputs at least the detected and measured amounts of mecA, SCCmec, and a *Staphylococcus aureus*-specific target gene sequence to determine whether MRSA is present in the sample, wherein the call algorithm creates an intermediate value from at least mecA and the *Staphylococcus aureus*-specific target gene sequence, wherein the call algorithm further uses a boundary space to determine the presence of MRSA, wherein the boundary space is defined using the intermediate value and SCCmec.

7. A method for creating a model that can be used to determine the presence of methicillin-resistant *Staphylococcus aureus* (MRSA) in an unknown sample, the method comprising:
   subjecting a set of known samples to conditions that will expose the nucleic acids of any bacteria present in the known samples, wherein the presence of MRSA is known for each sample in the set of known samples;
   amplifying and detecting the presence and amounts of at least mecA, orfX, and a *Staphylococcus aureus* (SA)-specific target gene sequence in the known samples;
   executing a call algorithm on a digital computer for each sample in the known samples, wherein the call algorithm uses as inputs the detected and measured amounts of mecA, orfX, and the *Staphylococcus aureus*-specific target gene sequence; and
   creating a model that can be used to determine whether MRSA is present in the unknown sample, wherein the model is created from the output of the call algorithm executed against the known samples, wherein the model uses a first boundary space to determine the presence of MRSA when the detected amount of orfX is below a threshold value, wherein the model uses a second boundary space to determine the presence of MRSA when the detected amount of orfX is above the threshold value.

8. A method for creating a model that can be used to determine the presence of methicillin-resistant *Staphylococcus aureus* (MRSA) in an unknown sample, the method comprising:
   subjecting a set of known samples to conditions that will expose the nucleic acids of any bacteria present in the known samples, wherein the presence of MRSA is known for each sample in the set of known samples;
   amplifying and detecting the presence and amounts of at least mecA, SCCmec, and a *Staphylococcus aureus* (SA)-specific target gene sequence in the known samples;
   executing a call algorithm on a digital computer for each sample in the known samples, wherein the call algorithm uses as inputs the detected and measured amounts of mecA, SCCmec, and the *Staphylococcus aureus*-specific target gene sequence; and
   creating a model that can be used to determine whether MRSA is present in the unknown sample, wherein the model is created from the output of the call algorithm executed against the known samples, wherein the model creates an intermediate value from at least the *Staphylococcus aureus*-specific target gene sequence and mecA, wherein the call algorithm further uses a boundary space to determine the presence of MRSA, wherein the boundary space is defined using the intermediate value and SCCmec.

9. The method of claim 1 wherein the *Staphylococcus aureus*-specific target gene sequence is femA.

10. The method of claim 1 wherein the first boundary space and the second boundary space are both elliptical boundary spaces.

11. The method of claim 10 wherein the first boundary space and the second boundary space have both undergone translations and angular displacement around an origin.

12. The method of claim 1 wherein the first boundary space and the second boundary space are both defined as a function of the measured amounts of mecA and the *Staphylococcus aureus*-specific target gene sequence.

13. The method of claim 1 wherein a cost function is used to find the optimal parameters for the first and second boundary spaces.

14. The method of claim 13 wherein the cost function is defined by the formula:

cost=$c_1$*FN#+$c_2$*FP#.

15. The method of claim 1 wherein the first boundary space and the second boundary space are functions defined using a neural network.

16. The method of claim 1 wherein the first boundary space and the second boundary space are functions defined using a genetic algorithm.

17. The method of claim 1 wherein the presence and amounts of at least mecA, orfX, and the *Staphylococcus aureus*-specific target gene sequence in the sample are detected by real-time PCR.

18. The method of claim 17 wherein the amounts of at least mecA, orfX, and the *Staphylococcus aureus*-specific target gene sequence are measured in cycles.

19. The method of claim 18 wherein the threshold value is approximately 45 cycles.

20. The method of claim 4 wherein the *Staphylococcus aureus*-specific target gene sequence is femA.

21. The method of claim 4 wherein the intermediate value is a defined as a function of mecA and SA, wherein the intermediate value is a weighted linear combination of mecA and SA is defined using the formula:

intermediate value=mecA*sin(−0.3)+SA*cos(−0.3).

22. The method of claim 4 wherein the first boundary space and the second boundary space are both defined as a function of the measured amounts of mecA and the *Staphylococcus aureus*-specific target gene sequence.

23. The method of claim 4 wherein a cost function is used to find the optimal parameters for the first and second boundary spaces.

24. The method of claim 23 wherein the cost function is defined by the formula:

cost=$c_1$*FN#+$c_2$*FP#.

25. The method of claim 4 wherein the first boundary space and the second boundary space are functions defined using a genetic algorithm.

26. The method of claim 4 wherein the presence and amounts of at least mecA, SCCmec, and the *Staphylococcus aureus*-specific target gene sequence in the sample are detected by real-time PCR.

27. The method of claim 26 wherein the amounts of at least mecA, SCCmec, and the *Staphylococcus aureus*-specific target gene sequence are measured in cycles.

* * * * *

SEQUENCE LISTING

<160> NUMBER OF SEQ ID NOS: 27

<210> SEQ ID NO 1
<211> LENGTH: 26
<212> TYPE: DNA
<213> ORGANISM: Artificial Sequence
<220> FEATURE:
<223> OTHER INFORMATION: synthetic PCR forward primer oligo ID
      OrfX-ISS/attBScc for-1 for orfX-ISS or SCCmec targets

<400> SEQUENCE: 1
tgagggttgt gttaattgag caagtg                                          26

<210> SEQ ID NO 2
<211> LENGTH: 26
<212> TYPE: DNA
<213> ORGANISM: Artificial Sequence
<220> FEATURE:
<223> OTHER INFORMATION: synthetic PCR forward primer oligo ID
      OrfX-ISS/attBScc for-2 for orfX-ISS or SCCmec targets

<400> SEQUENCE: 2
tgcgggttgt gttaattgaa caagtg                                          26

<210> SEQ ID NO 3
<211> LENGTH: 28
<212> TYPE: DNA
<213> ORGANISM: Artificial Sequence
<220> FEATURE:
<223> OTHER INFORMATION: synthetic PCR reverse primer oligo ID
      mecII512-1-sccmec-3 for orfX-ISS or SCCmec targets

<400> SEQUENCE: 3 tcactttta ttcttcaaag atttgagc                                         28

<210> SEQ ID NO 4
<211> LENGTH: 33
<212> TYPE: DNA
<213> ORGANISM: Artificial Sequence
<220> FEATURE:
<223> OTHER INFORMATION: synthetic PCR reverse primer oligo ID
      primer11-1-sccmec-7 for orfX-ISS or SCCmec targets

<400> SEQUENCE: 4
aaattgctac taaagaggat atggaaaacc atc                                  33

<210> SEQ ID NO 5
<211> LENGTH: 29
<212> TYPE: DNA
<213> ORGANISM: Artificial Sequence
<220> FEATURE:
<223> OTHER INFORMATION: synthetic PCR reverse primer oligo ID primer
      12-sccmec-8 for orfX-ISS or SCCmec targets

<400> SEQUENCE: 5
ctctgcttta tattataaaa ttacggctg                                       29

```
<210> SEQ ID NO 6
<211> LENGTH: 33
<212> TYPE: DNA
<213> ORGANISM: Artificial Sequence
<220> FEATURE:
<223> OTHER INFORMATION: synthetic PCR reverse primer oligo ID
      newtypeiii-1-sccmec-14 for orfX-ISS or SCCmec targets

<400> SEQUENCE: 6
cgtatgatat tgcaaggtat aatccaatat ttc                                 33

<210> SEQ ID NO 7
<211> LENGTH: 28
<212> TYPE: DNA
<213> ORGANISM: Artificial Sequence
<220> FEATURE:
<223> OTHER INFORMATION: synthetic PCR reverse primer oligo ID
      typeIVc-sccmec-2 for orfX-ISS or SCCmec targets

<400> SEQUENCE: 7
cttgaaatga aagactgcgg aggctaac                                        28

<210> SEQ ID NO 8
<211> LENGTH: 30
<212> TYPE: DNA
<213> ORGANISM: Artificial Sequence
<220> FEATURE:
<223> OTHER INFORMATION: synthetic PCR reverse primer oligo ID
      NEWPRIMERS for orfX-ISS or SCCmec targets

<400> SEQUENCE: 8
tgagcttttt ccactcccat ttcttccaaa                                      30

<210> SEQ ID NO 9
<211> LENGTH: 32
<212> TYPE: DNA
<213> ORGANISM: Artificial Sequence
<220> FEATURE:
<223> OTHER INFORMATION: synthetic PCR reverse primer oligo ID
      SCCmec-4nV for orfX-ISS or SCCmec targets

<400> SEQUENCE: 9
gcaattcaca taaacctcat atgttctgat ac                                   32

<210> SEQ ID NO 10
<211> LENGTH: 32
<212> TYPE: DNA
<213> ORGANISM: Artificial Sequence
<220> FEATURE:
<223> OTHER INFORMATION: synthetic PCR reverse primer oligo ID SCCmec-3n
      for orfX-ISS or SCCmec targets

<400> SEQUENCE: 10
cattcattca tccaccctaa acttaatctt tc                                   32

<210> SEQ ID NO 11
<211> LENGTH: 34
<212> TYPE: DNA
<213> ORGANISM: Artificial Sequence
<220> FEATURE:
<223> OTHER INFORMATION: synthetic PCR reverse primer oligo ID SCCmec-5n
      for orfX-ISS or SCCmec targets

<400> SEQUENCE: 11
tatggaaatc catctctact ttattgtttt cttc                                 34

<210> SEQ ID NO 12
```

-continued

```
<211> LENGTH: 32
<212> TYPE: DNA
<213> ORGANISM: Artificial Sequence
<220> FEATURE:
<223> OTHER INFORMATION: synthetic PCR reverse primer oligo ID SCCmec-6n
      for orfX-ISS or SCCmec targets

<400> SEQUENCE: 12
aatatttcat atatgtaatt cctccacatc tc                                    32

<210> SEQ ID NO 13
<211> LENGTH: 32
<212> TYPE: DNA
<213> ORGANISM: Artificial Sequence
<220> FEATURE:
<223> OTHER INFORMATION: synthetic PCR reverse primer oligo ID SE-7-11
      for orfX-ISS or SCCmec targets

<400> SEQUENCE: 13
ctatttctgt aatacttaaa accttttctt cc                                    32

<210> SEQ ID NO 14
<211> LENGTH: 35
<212> TYPE: DNA
<213> ORGANISM: Artificial Sequence
<220> FEATURE:
<223> OTHER INFORMATION: synthetic PCR reverse primer oligo ID SE-17 for
      orfX-ISS or SCCmec targets

<400> SEQUENCE: 14
ccgtatgatt catattaaaa tgaatcatac ggagg                                 35

<210> SEQ ID NO 15
<211> LENGTH: 31
<212> TYPE: DNA
<213> ORGANISM: Artificial Sequence
<220> FEATURE:
<223> OTHER INFORMATION: synthetic PCR reverse primer oligo ID SE-13 for
      orfX-ISS or SCCmec targets

<400> SEQUENCE: 15
cttcttatga aatgtctttt ttcacttatc c                                     31

<210> SEQ ID NO 16
<211> LENGTH: 30
<212> TYPE: DNA
<213> ORGANISM: Artificial Sequence
<220> FEATURE:
<223> OTHER INFORMATION: synthetic PCR TaqMan probe oligo ID orfx
      probe-2 for orfX-ISS or SCCmec targets

<400> SEQUENCE: 16
atgcttctcc tcgcataatc ttaaaygctc                                       30

<210> SEQ ID NO 17
<211> LENGTH: 30
<212> TYPE: DNA
<213> ORGANISM: Artificial Sequence
<220> FEATURE:
<223> OTHER INFORMATION: synthetic PCR TaqMan probe oligo ID ORFX
      PROBE-1 for orfX-ISS or SCCmec targets

<400> SEQUENCE: 17
acgcttctcc acgcataatc ttaaatgctc                                       30

<210> SEQ ID NO 18
<211> LENGTH: 30
<212> TYPE: DNA
```

-continued

```
<213> ORGANISM: Artificial Sequence
<220> FEATURE:
<223> OTHER INFORMATION: synthetic PCR Taqman probe oligo ID ORFX PROBE
      for orfX-ISS or SCCmec targets

<400> SEQUENCE: 18
acgcctctcc tcgcataatc ttaaatgctc                                    30

<210> SEQ ID NO 19
<211> LENGTH: 29
<212> TYPE: DNA
<213> ORGANISM: Artificial Sequence
<220> FEATURE:
<223> OTHER INFORMATION: synthetic PCR forward primer oligo ID femA-3
      forward primer for femA target

<400> SEQUENCE: 19
gaccgttata atttctatgg tgttagtgg                                     29

<210> SEQ ID NO 20
<211> LENGTH: 27
<212> TYPE: DNA
<213> ORGANISM: Artificial Sequence
<220> FEATURE:
<223> OTHER INFORMATION: synthetic PCR reverse primer oligo ID femA-3
      reverse primer for femA target

<400> SEQUENCE: 20
gtcaccaaca tattcaataa tttcagc                                       27

<210> SEQ ID NO 21
<211> LENGTH: 26
<212> TYPE: DNA
<213> ORGANISM: Artificial Sequence
<220> FEATURE:
<223> OTHER INFORMATION: synthetic PCR TaqMan probe oligo ID
      femA-sa-probe for femA target

<400> SEQUENCE: 21
acagaagatg ctgaagatgc tggtgt                                        26

<210> SEQ ID NO 22
<211> LENGTH: 27
<212> TYPE: DNA
<213> ORGANISM: Artificial Sequence
<220> FEATURE:
<223> OTHER INFORMATION: synthetic PCR forward primer oligo ID mecA-2
      forward primer for mecA target

<400> SEQUENCE: 22
gcagaaagac caaagcatac atattga                                       27

<210> SEQ ID NO 23
<211> LENGTH: 24
<212> TYPE: DNA
<213> ORGANISM: Artificial Sequence
<220> FEATURE:
<223> OTHER INFORMATION: synthetic PCR reverse primer oligo ID mecA-2
      reverse primer for mecA target

<400> SEQUENCE: 23
gcctatctca tatgctgttc ctgt                                          24

<210> SEQ ID NO 24
<211> LENGTH: 26
<212> TYPE: DNA
<213> ORGANISM: Artificial Sequence
<220> FEATURE:
```

-continued

```
<223> OTHER INFORMATION: synthetic PCR TaqMan probe oligo ID mecAprobe
      for mecA target

<400> SEQUENCE: 24
agaccgaaac aatgtggaat tggcca                                          26

<210> SEQ ID NO 25
<211> LENGTH: 24
<212> TYPE: DNA
<213> ORGANISM: Artificial Sequence
<220> FEATURE:
<223> OTHER INFORMATION: synthetic PCR IC forward primer oligo ID
      Sfforwardnew for S. felis (IC) target

<400> SEQUENCE: 25
tgccaatgta gatagtcttc caga                                            24

<210> SEQ ID NO 26
<211> LENGTH: 22
<212> TYPE: DNA
<213> ORGANISM: Artificial Sequence
<220> FEATURE:
<223> OTHER INFORMATION: synthetic PCR IC reverse primer oligo ID
      sfreversenew for S. felis (IC) target

<400> SEQUENCE: 26
aagtgcccag aagaatgagt gg                                              22

<210> SEQ ID NO 27
<211> LENGTH: 26
<212> TYPE: DNA
<213> ORGANISM: Artificial Sequence
<220> FEATURE:
<223> OTHER INFORMATION: synthetic PCR IC probe oligo ID fSfelis for S.
      felis (IC) target

<400> SEQUENCE: 27
accgccacca ttattacgta cagctg                                          26
```